United States Patent
Vieceli et al.

(10) Patent No.: US 11,835,460 B2
(45) Date of Patent: *Dec. 5, 2023

(54) SYSTEM AND METHOD WITH FIDUCIALS HAVING OFFSET LAYOUTS

(71) Applicant: Illumina, Inc., San Diego, CA (US)

(72) Inventors: John S. Vieceli, Encinitas, CA (US); Alex Nemiroski, San Diego, CA (US); Paul Belitz, San Diego, CA (US); Robert Langlois, San Diego, CA (US); M. Shane Bowen, Encinitas, CA (US); Danny Yuan Chan, San Diego, CA (US); Bala Murali K. Venkatesan, San Francisco, CA (US); Hui Han, San Diego, CA (US); Kevan Samiee, San Diego, CA (US); Stephen Tanner, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 648 days.

This patent is subject to a terminal disclaimer.

(21) Appl. No.: 16/482,638

(22) PCT Filed: Jan. 31, 2018

(86) PCT No.: PCT/US2018/016189
§ 371 (c)(1),
(2) Date: Jul. 31, 2019

(87) PCT Pub. No.: WO2018/144574
PCT Pub. Date: Aug. 9, 2018

(65) Prior Publication Data
US 2020/0011800 A1    Jan. 9, 2020

(30) Foreign Application Priority Data
Feb. 1, 2017 (GB) .................. 1701686

(51) Int. Cl.
*G01N 21/64* (2006.01)
*B01J 19/00* (2006.01)
*C12Q 1/6837* (2018.01)

(52) U.S. Cl.
CPC ...... *G01N 21/6456* (2013.01); *B01J 19/0046* (2013.01); *C12Q 1/6837* (2013.01);
(Continued)

(58) Field of Classification Search
CPC ........... G01N 21/6456; G01N 21/6452; G01N 2021/6419; G01N 2021/6421;
(Continued)

(56) References Cited

U.S. PATENT DOCUMENTS 5,528,050 A    6/1996    Miller et al.
5,719,391 A    2/1998    Kain
(Continued)

FOREIGN PATENT DOCUMENTS

CN    1668923    9/2005
CN    101799422    8/2010
(Continued)

OTHER PUBLICATIONS

Translation of JP2006324224A, Karantaru, Kariru, Nov. 30, 2006 (Year: 2006).*
(Continued)

*Primary Examiner* — Jill A Warden
*Assistant Examiner* — Henry H Nguyen
(74) *Attorney, Agent, or Firm* — Dierker & Kavanaugh, P.C.

(57) ABSTRACT

Fiducial markers are provided on patterned arrays of the type that may be used for molecular analysis, such as sequencing. The fiducials may have configurations and layouts that enhance their detection in image or detection data, that facilitate or improve processing, that provide
(Continued)

encoding of useful information, and so forth. Examples of the fiducials may include offset layouts that may be useful in detecting the fiducials in different types and approaches in imaging, and that may help to distinguish regions of the array from one another in image data.

13 Claims, 11 Drawing Sheets

(52) U.S. Cl.
CPC ... *G01N 21/6452* (2013.01); *B01J 2219/0056* (2013.01); *B01J 2219/00317* (2013.01); *B01J 2219/00529* (2013.01); *B01J 2219/00547* (2013.01); *B01J 2219/00549* (2013.01); *B01J 2219/00576* (2013.01); *B01J 2219/00608* (2013.01); *B01J 2219/00648* (2013.01); *B01J 2219/00722* (2013.01); *B01L 2300/021* (2013.01); *G01N 2021/6419* (2013.01); *G01N 2021/6421* (2013.01); *H01J 2237/24578* (2013.01)

(58) Field of Classification Search
CPC .......... B01J 19/0046; B01J 2219/00317; B01J 2219/00547; B01J 2219/00549; B01J 2219/0056; B01J 2219/00608; B01J 2219/00722; B01J 2219/00529; B01J 2219/00576; B01J 2219/00648; B01J 2219/00659; C12Q 1/6837; H01J 2237/24578; B01L 3/5085; B01L 2200/025; B01L 2300/021
See application file for complete search history.

(56) References Cited

U.S. PATENT DOCUMENTS

| | | | |
|---|---|---|---|
| 5,900,640 A | 5/1999 | Ogura |
| 5,986,256 A | 11/1999 | Yagi |
| 6,023,071 A | 2/2000 | Ogura et al. |
| 6,023,540 A | 2/2000 | Walt et al. |
| 6,258,326 B1 | 7/2001 | Modlin |
| 6,306,643 B1 | 10/2001 | Gentalen et al. |
| 6,355,431 B1 | 3/2002 | Chee et al. |
| 6,362,004 B1 | 3/2002 | Noblett |
| 6,673,315 B2 | 1/2004 | Sheridan et al. |
| 6,770,441 B2 | 8/2004 | Dickinson et al. |
| 7,200,254 B2 | 4/2007 | Kira et al. |
| 7,231,063 B2 | 6/2007 | Naimark et al. |
| 7,307,802 B2 | 12/2007 | Unger |
| 7,329,860 B2 | 2/2008 | Feng et al. |
| 7,405,281 B2 | 7/2008 | Xu et al. |
| 7,499,806 B2 | 3/2009 | Kermani et al. |
| 7,604,984 B2 | 10/2009 | Frutos et al. |
| 7,629,173 B2 | 12/2009 | Gollier et al. |
| 7,769,548 B2 | 8/2010 | Garcia |
| 7,835,871 B2 | 11/2010 | Kain et al. |
| 7,941,279 B2 | 5/2011 | Hwang et al. |
| 7,960,702 B2 | 6/2011 | Sutko et al. |
| 8,039,817 B2 | 10/2011 | Feng et al. |
| 8,040,515 B2 | 10/2011 | Sonehara et al. |
| 8,241,573 B2 | 8/2012 | Banerjee et al. |
| 8,343,746 B2 | 1/2013 | Rank et al. |
| 8,680,483 B2 | 3/2014 | Haga et al. |
| 8,753,898 B2 | 6/2014 | Machida et al. |
| 8,865,459 B2 | 10/2014 | Narahara et al. |
| 8,929,630 B2 | 1/2015 | Fu |
| 8,951,781 B2 | 2/2015 | Reed et al. |
| 8,965,076 B2 | 2/2015 | Garcia et al. |
| 9,012,022 B2 | 4/2015 | George et al. |
| 9,013,690 B1 | 4/2015 | Chou et al. |
| 9,193,996 B2 | 11/2015 | Buermann et al. |
| 9,213,176 B2 | 12/2015 | Pertsinidis et al. |
| 9,256,935 B2 | 2/2016 | Bonanni et al. |
| 9,285,321 B2 | 3/2016 | Kawamuki |
| 9,329,174 B2 | 5/2016 | Noji et al. |
| 9,382,585 B2 | 7/2016 | Oliphant et al. |
| 9,404,737 B2 | 8/2016 | Segale et al. |
| 9,512,422 B2 | 12/2016 | Barnard et al. |
| 9,624,537 B2 | 4/2017 | Huber et al. |
| 9,767,342 B2 | 9/2017 | Stern et al. |
| 9,823,197 B2 | 11/2017 | Nagino et al. |
| 9,901,923 B2 | 2/2018 | Lee et al. |
| 9,976,174 B2 | 5/2018 | Rawlings et al. |
| 10,059,992 B2 | 8/2018 | Dehlinger et al. |
| 10,082,497 B2 | 9/2018 | Di Carlo et al. |
| 10,094,780 B2 | 10/2018 | Tanaka |
| 10,145,795 B2 | 12/2018 | Saitou |
| 10,204,401 B2 | 2/2019 | Tanaka |
| 10,215,998 B2 | 2/2019 | Leonberger et al. |
| 10,241,028 B2 | 3/2019 | Rowe et al. |
| 10,247,672 B2 | 4/2019 | Betzig et al. |
| 10,417,790 B2 | 9/2019 | Ikami et al. |
| 10,540,783 B2 | 1/2020 | Vieceli et al. |
| 10,598,597 B2 | 3/2020 | Bahlman et al. |
| 10,761,028 B2 | 9/2020 | Raphael et al. |
| 10,768,105 B1 | 9/2020 | Mohan et al. |
| 10,890,528 B2 | 1/2021 | Lizuka et al. |
| 10,895,534 B2 | 1/2021 | Finkelstein et al. |
| 11,067,535 B2 | 7/2021 | Iizuka et al. |
| 11,249,025 B2* | 2/2022 | Vieceli ............... G01N 21/6456 |
| 11,262,307 B2* | 3/2022 | Vieceli ................ G01N 21/645 |
| 2002/0150909 A1 | 10/2002 | Stuelpnagel et al. |
| 2003/0027342 A1 | 2/2003 | Sheridan et al. |
| 2003/0152256 A1 | 8/2003 | Kira et al. |
| 2004/0028258 A1 | 2/2004 | Naimark et al. |
| 2004/0060987 A1 | 4/2004 | Green |
| 2004/0150217 A1 | 8/2004 | Heffelfinger et al. |
| 2005/0017191 A1 | 1/2005 | Montagu et al. |
| 2006/0041384 A1 | 2/2006 | Kermani et al. |
| 2007/0031856 A1 | 2/2007 | Hong |
| 2007/0202543 A1 | 8/2007 | Gollier et al. |
| 2008/0281527 A1 | 11/2008 | Garcia et al. |
| 2009/0112482 A1 | 4/2009 | Sandstrom |
| 2010/0204057 A1 | 8/2010 | Lee et al. |
| 2010/0262374 A1 | 10/2010 | Hwang et al. |
| 2010/0296727 A1 | 11/2010 | Stern et al. |
| 2011/0009278 A1 | 1/2011 | Kain et al. |
| 2011/0009289 A1 | 1/2011 | Gentalen et al. |
| 2011/0092389 A1 | 4/2011 | Dickinson et al. |
| 2012/0002031 A1 | 1/2012 | Pertsinidis et al. |
| 2013/0091176 A1* | 4/2013 | Harris .................. B01J 19/0046 707/E17.049 |
| 2014/0179554 A1 | 6/2014 | Svoboda et al. |
| 2014/0243224 A1 | 8/2014 | Barnard et al. |
| 2015/0125053 A1 | 5/2015 | Vieceli et al. |
| 2015/0154748 A1 | 6/2015 | Bonanni et al. |

FOREIGN PATENT DOCUMENTS

| | | |
|---|---|---|
| CN | 101813617 | 8/2010 |
| CN | 202379991 | 8/2012 |
| CN | 105717078 | 6/2016 |
| EP | 2933017 | 10/2015 |
| EP | 3037862 | 6/2016 |
| JP | 2006324224 A * | 11/2006 |
| WO | WO 02/18945 | 3/2002 |
| WO | WO 2004025563 | 3/2004 |
| WO | WO 2004065995 | 8/2004 |
| WO | 2008016335 A1 | 2/2008 |
| WO | WO 2008096318 | 8/2008 |
| WO | WO 2015054292 | 4/2015 |
| WO | WO 2015082196 | 6/2015 |

OTHER PUBLICATIONS

Russom et al., "SNP Analysis by Dynamic Allele Specific Hybridization on Patterned Monolayers of Beads", 2003, 7th International Conference on Miniaturized Chemical and Biochemical Analysis Systems (Year: 2003).*

(56) References Cited

OTHER PUBLICATIONS

International Search Report and Written Opinion for International Application No. PCT/US2018/016132 dated May 14, 2018, 24 pages.
International Search Report and Written Opinion for International Application No. PCT/US2018/016175 dated Apr. 27, 2018, 17 pages.
International Search Report and Written Opinion for International Application No. PCT/US2018/016180 dated May 11, 2018, 16 pages.
International Search Report and Written Opinion for International Application No. PCT/US2018/016189 dated May 21, 2018, 17 pages.
International Search Report and Written Opinion for International Application No. PCT/US2018/016205 dated May 11, 2018, 17 pages.
Pregibon, D. C. et al., "Multifunctional Encoded Particles for High-Throughput Biomolecule Analysis", Science, vol. 315, No. 5817, 2007, p. 1393-1396.
Didier, F et al. "Rapid, Sensitive and Real-Time Multiplexing Platform for the Analysis of Protein and Nucleic-Acid Biomarkers" Analytical Chem. vol. 87, No. 3, 2015, p. 1582-89.

\* cited by examiner

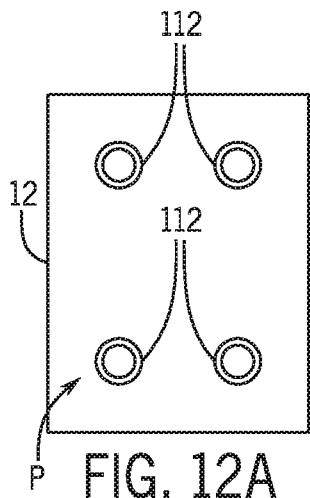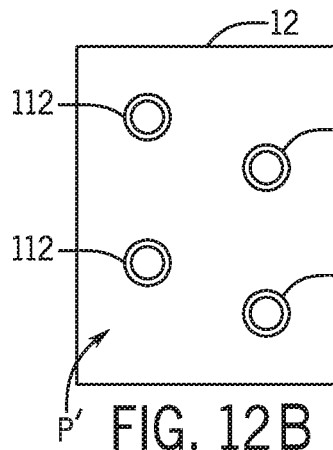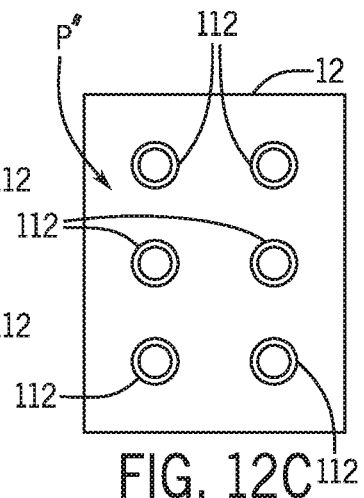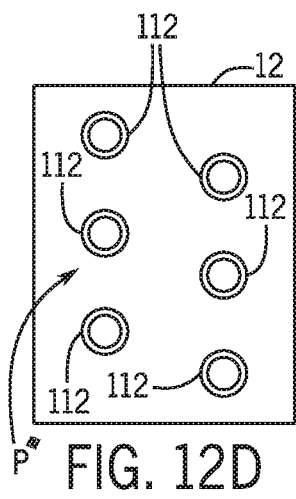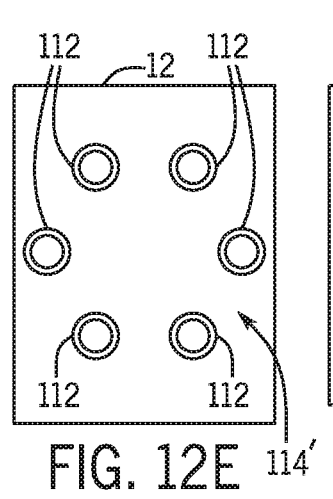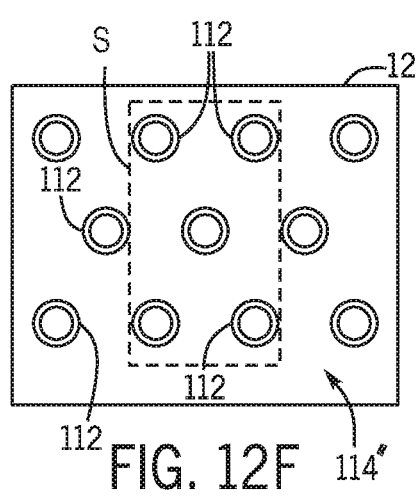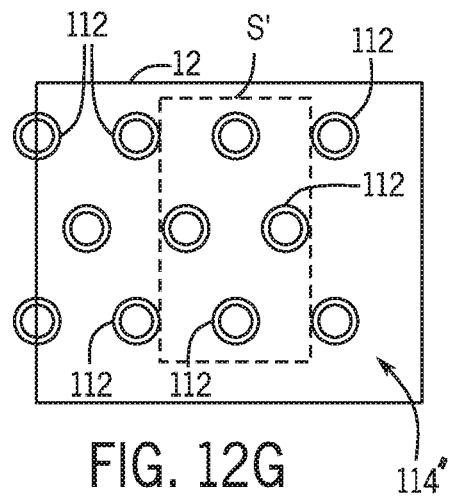

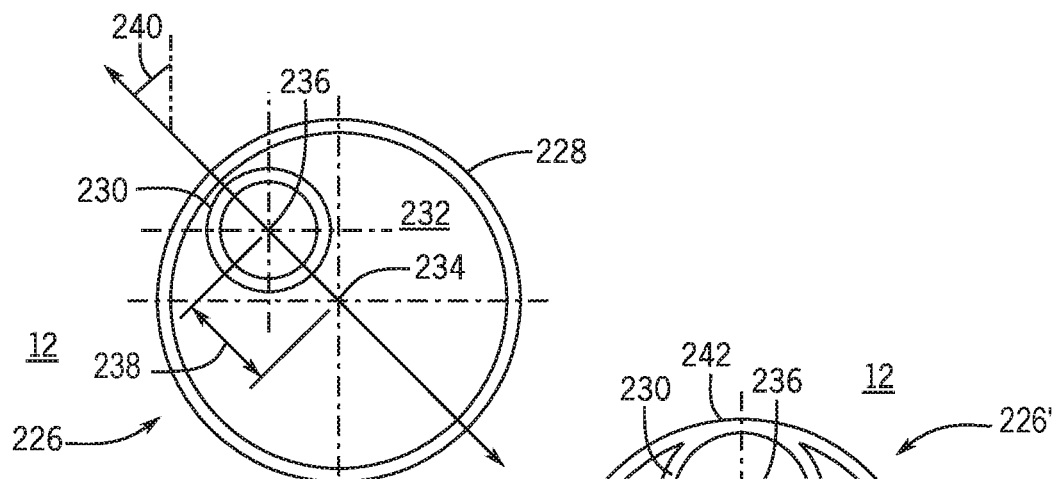
FIG. 19A
FIG. 19B
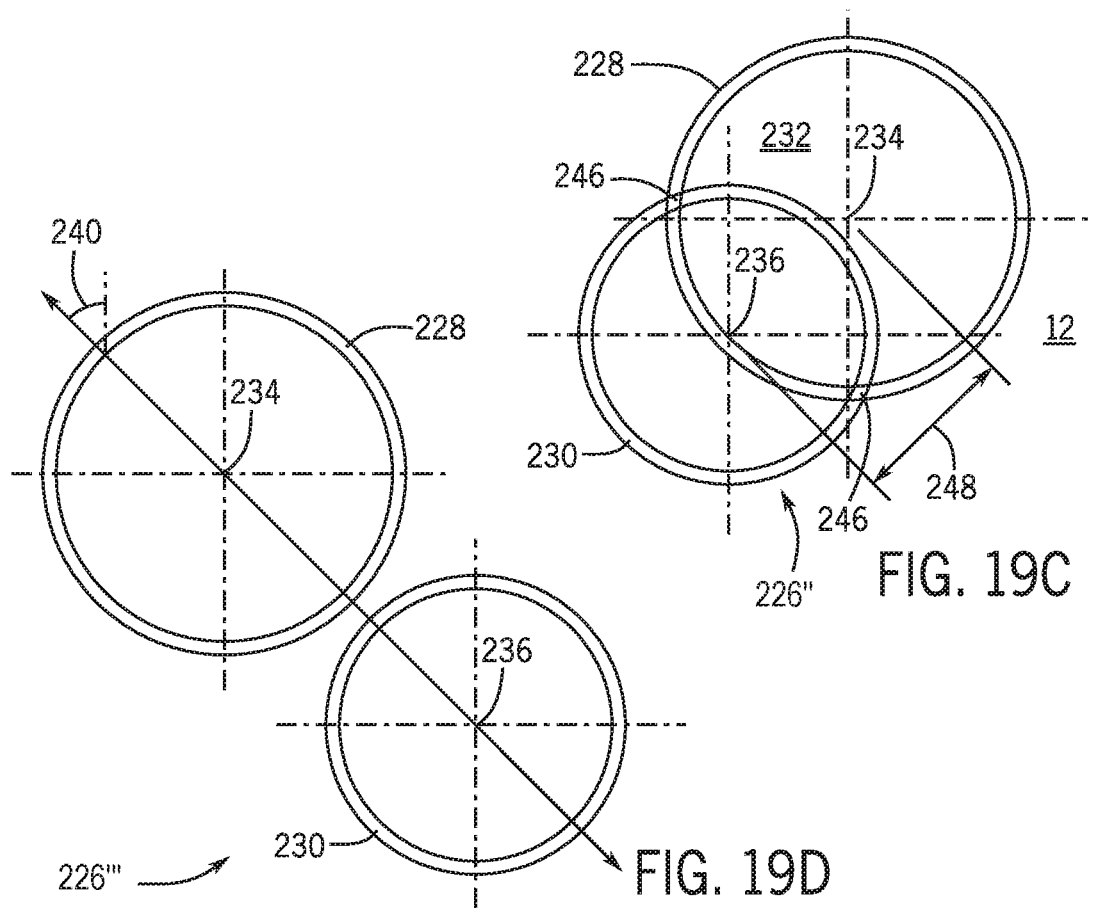
FIG. 19C
FIG. 19D

SYSTEM AND METHOD WITH FIDUCIALS HAVING OFFSET LAYOUTS

CROSS-REFERENCE TO RELATED APPLICATIONS

This application claims priority to Great Britain (GB) Patent Application Number 1701686.6, filed Feb. 1, 2017, the contents of which is incorporated by reference herein in its entirety.

BACKGROUND

An increasing number of applications have been developed for patterned arrays. Such patterned arrays may, for example, support deoxyribonucleic acid (DNA) and ribonucleic acid (RNA) probes. These are specific for nucleotide sequences present in genes in humans and other organisms. In some applications, for example, individual DNA and RNA probes can be attached at small locations in a geometric grid (or randomly) on a patterned array support. A test sample, such as from a known or unknown person or organism, can be exposed to the grid, such that complementary genes of fragments hybridize to probes at the individual sites in the array. The array can then be examined, such as by scanning specific frequencies of light over the sites to identify which genes or fragments in the sample are present, often by fluorescence of the sites at which genes or fragments are located. Detection of the features of the array to which fragments from the sample are bound can be used to identify molecular sequences present in the sample. Nucleic acid arrays may also be used for basic genetic sequencing. In general, genetic sequencing consists of determining the nucleic acid or the order of nucleotides in a length of genetic material. The technology is continuing to evolve and improve, and ever larger nucleic acid samples, such as more complex genomes (as well as other analytes), are being sequenced on arrays.

For these and other applications of nucleic acid arrays, improvements have also been made in detection hardware and programming. For example, improvements in imaging systems allow for faster, more accurate and higher resolution scanning and imaging, such as through the use of line-scanning and confocal control of imaging optics. However, in one example, as the density of features in the arrays increases, and the size of the features decreases, and the overall size of the arrays expand, accurate detection becomes problematic. With the number and density of sites on the arrays increasing, challenges include the ability to accurately locate the sites, align or index the sites in successive cycles of sequencing and imaging, and avoiding issues that might confuse comparison of successive images or image data (needed to determine the sequences present at the sites of the array). The economic costs and time involved in detection and image processing may also become problematic.

SUMMARY

A first aspect of the present disclosure provides an array comprising a support having locations that, in operation, receive biological samples differing from one another to respond differently in successive cycles of fluorescent imaging, and fiducial features on the support having a fluorescent material that responds in the successive cycles of fluorescent imaging, wherein the fiducial features are disposed in rows that are offset with respect to one another, wherein in the offset rows, fiducials of a first row do not align with fiducials of an adjacent second row, relative to a line perpendicular to the first row and the adjacent second row.

In an example of the first aspect, the fiducial features form a triangular pattern.

In an example of the first aspect, the fiducial features form a hexagonal pattern. As one example, the fiducial features form the hexagonal pattern, and the hexagonal pattern includes a fiducial feature within a hexagon.

In an example of the first aspect, the fiducial features are disposed in a density to provide at least four of the fiducial features in an image area of a sequencing instrument.

In an example of the first aspect, the fiducial features are disposed in a density to provide at least five of the fiducial features in an image area of a sequencing instrument.

In an example of the first aspect, the fiducial features are disposed in a density to provide at least six of the fiducial features in an image area of a sequencing instrument.

In an example of the first aspect, the successive cycles of fluorescent imaging are performed utilizing light at at least two different wavelengths, and wherein the fluorescent material of the fiducial features is responsive to both of the at least two different wavelengths.

In an example of the first aspect, the fiducial features comprise at least one depression and objects disposed in the at least one depression, the objects comprising the fluorescent material. As an example, the objects disposed in the at least one depression are too large to be stably received in the locations of the support that receive the biological samples.

In an example of the first aspect, the locations are disposed in a repeating pattern on the support.

In an example of the first aspect, the support comprises a plurality of areas of the locations, and wherein one of the fiducial features is provided in each of the plurality of areas.

In an example of the first aspect, the biological samples comprise nucleic acid sequences.

In an example of the first aspect, at least one of the fiducial features comprises a plurality of non-concentric shapes.

In an example of the first aspect, at least one of the fiducial features is structured to produce image data encoding information.

An example of the first aspect further comprises at least one additional fiducial feature that is formed in or on the support and is optically reflective to, during imaging, return at least a portion of incident radiation for locating, adjusting the location of, or registering the support or the locations.

It is to be understood that any features of the first aspect of the array may be combined together in any desirable manner and/or configuration.

A second aspect of this disclosure also provides a method comprising disposing biological samples at locations on a support, the biological samples differing from one another to respond differently in successive cycles of fluorescent imaging, wherein the locations are disposed in a plurality of swaths on the support, and disposing fiducial features on the support, each of the fiducial features comprising a fluorescent material that responds in the successive cycles of fluorescent imaging, wherein the fiducial features are disposed in rows that are offset with respect to one another, and wherein in the offset rows, fiducials of a first row do not align with fiducials of an adjacent second row, relative to a line perpendicular to the first row and adjacent second row.

An example of the second aspect further comprises imaging the biological samples and the fiducial features in the successive cycles of fluorescent imaging at different wavelengths of light to produce image data that encodes fluorescent signals produced by the biological samples and the fiducial features.

In an example of the second aspect, between each successive cycle of fluorescent imaging, a tag is removed from the biological sample at each location, and an additional biological component is added to each biological sample at each location, the additional biological components having tags that respond to the successive cycle of fluorescent imaging.

It is to be understood that any features of this second aspect, or method, may be combined together in any desirable manner. Moreover, it is to be understood that any combination of features of this method and/or of the first aspect (array), may be used together, and/or combined with any of the examples disclosed herein.

A third aspect of this disclosure provides a method comprising accessing image data encoding successive images of biological samples disposed at locations on a support, the biological samples differing from one another to respond differently in successive cycles of fluorescent imaging, wherein the support comprises a plurality of fiducial features, the fiducial features comprising a fluorescent material that responds in the successive cycles of fluorescent imaging, wherein the fiducial features are disposed in rows that are offset with respect to one another, and wherein in the offset rows, fiducials of a first row do not align with fiducials of an adjacent second row, relative to a line perpendicular to the first row and the adjacent second row; registering, for the successive images, the locations on the support by reference to the fiducial features; and processing the registered successive images to transform data derived from the successive images to sequence data.

It is to be understood that any features of this third aspect, or method, may be combined together in any desirable manner. Moreover, it is to be understood that any combination of features of this method and/or of the second aspect (other method) and/or of the first aspect (array), may be used together, and/or combined with any of the examples disclosed herein.

Still further, it is to be understood that any features of any of the arrays and/or of any of the methods may be combined together in any desirable manner, and/or may be combined with any of the examples disclosed herein.

BRIEF DESCRIPTION OF THE DRAWINGS

These and other features and aspects of the present techniques will become better understood when the following detailed description is read with reference to the accompanying drawings in which like characters represent like parts throughout the drawings, wherein:

FIGS. 12A-12G are diagrammatic representations of example layouts of fiducials that allow for improved location and processing;

FIG. 19A-19D are detailed views of example fiducials comprising two shapes that are non-concentric and encoding information, such as by a directional offset;

DETAILED DESCRIPTION

Figure 1:
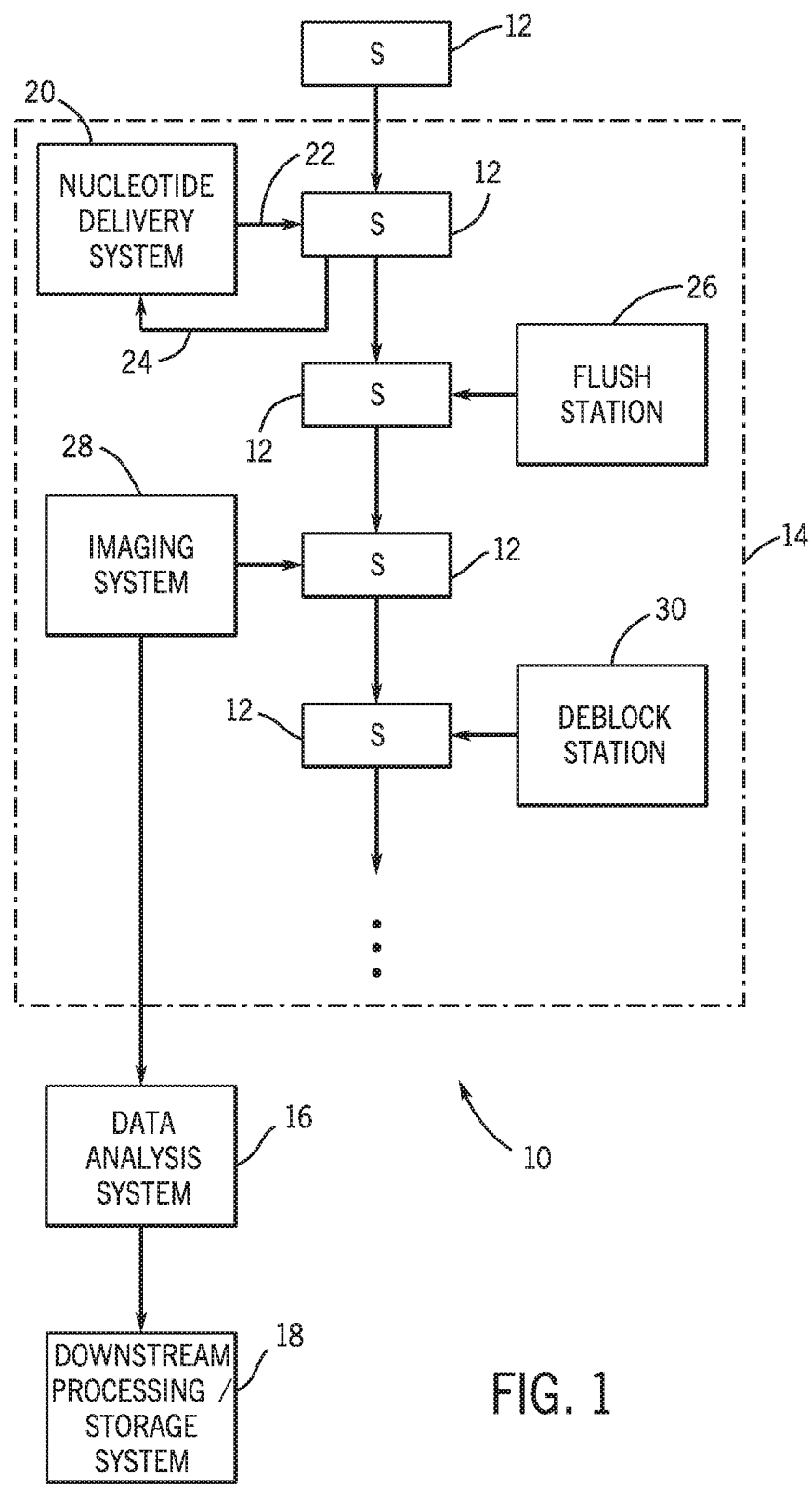
FIG. 1 is a diagrammatical overview of a patterned array imaging and image processing system, such as for biological samples, employing aspects of the present techniques.

This disclosure provides methods and systems for processing, imaging, and image data analysis that are useful for locating features of patterned arrays. The systems and methods may be used to register multiple images of such patterned arrays. Relevant to the present techniques are patterned arrays, the processing of which produces image data (or any other form of detection output of sites on the array) of analytical arrays, such as those used for the analysis of biological samples. Such arrays may contain repeating patterns of features that are to be resolved at sub-micron resolution ranges, for which the methods and systems of the present disclosure are well suited. Although the systems and methods set forth herein provide advantages when analyzing regular patterns of features, it will be understood that they can be used for random distributions of features as well. As discussed below, in many applications, the material to be imaged and analyzed will be located on one or more surfaces of one or more supports, such as a glass material. Beads or other locating devices may be used at sites to bind or anchor (or to otherwise locate) segments of material to be processed (e.g., hybridized, combined with additional molecules, imaged, and analyzed). In some cases, the molecules to be processed may be located randomly or pseudo-randomly on the support. Fiducial markers, or simply "fiducials" are located at known locations with respect to the sites, such as on or in the one or more supports, to assist in locating the support in the system (e.g., for imaging), and for locating the sites in subsequent image data.

It may be noted that as used in the present disclosure, a "patterned array" may include a microarray, a nanoarray, a sequencing array formed as a patterned flow cell, and so forth. Such devices comprise sites at which analytes may be located for processing and analysis. In practice, the sites may be disposed in a repeating pattern, a non-repeating pattern, or in a random arrangement on one or more surfaces of a support, which itself may comprise a flow cell as discussed below. For simplicity, all such devices are referred to and should be understood as included in the term "patterned array" or sometimes simply as "array".

The systems and methods of the present disclosure are robust to changes in characteristics of the features in the pattern or layout of the sites. The changes may manifest as different signal properties detected for one or more features in different images. For example, in a nucleic acid sequencing technique, an array of nucleic acids is subjected to several cycles of biochemical processing and imaging. In some examples, each cycle can result in one of four different labels being detected at each feature, depending upon the nucleotide base that is processed biochemically in that cycle. In such examples, multiple (e.g., four) different images are obtained at a given cycle and each feature will be detected in the images. In one example, alignment of the images for a given cycle presents unique challenges since features that are detected in one image may appear dark in the other images. Furthermore, sequencing includes multiple cycles, and alignment of features represented in image data from successive cycles is used to determine the sequence of nucleotides at each site based on the sequence of labels detected at the respective site. Improper registration of the images within a cycle or improper registration of images across different cycles can adversely affect sequence analysis. For example, methods that employ regular patterns may be susceptible to walk-off errors during image analysis. In one example, a walk-off error occurs when two overlaid images are offset by one or more repeat units of the pattern, such that the patterns appear to overlap but features that are neighbors in the different patterns are improperly correlated in the overlay.

As used herein, the term "fiducial" is intended to mean a distinguishable point of reference in or on an object, such as a support or substrate with sites for molecular materials to be analyzed, as well as in image data of the object. The point of reference can be, for example, a mark, an object, shape, edge, area, irregularity, channel, pit, post, or, as in many cases, a collection of features at known locations that can be used as a reference. The point of reference can be detected in an image of the object or in another data set derived from detecting (e.g., imaging) the object. The point of reference can be specified by an X and/or Y coordinate in a plane of the object (e.g., one or more surfaces of the patterned array). Alternatively or additionally, the point of reference can be specified by a Z coordinate that is orthogonal to the X-Y plane, for example, being defined by the relative locations of the object and a detector. One or more coordinates for a point of reference can be specified relative to one or more other features of an object or of an image or other data set derived from the object.

Several examples will be described below with respect to fiducials, their form, their configuration, and their use in systems and methods of analysis. It will be understood that systems are also provided for carrying out the methods in an automated or semi-automated way, and such systems will include a processor; a data storage device; and a program for image analysis, the program including instructions for carrying out one or more of the methods discussed below. Accordingly, the methods set forth herein can be carried out on a computer, for example, having components and algorithms needed for that purpose.

The methods and systems set forth herein are useful for analyzing any of a variety of materials, such as biological samples and molecules, which may be on or in a variety of objects. Useful objects are solid supports or solid-phase surfaces with attached analytes. The methods and systems set forth may provide advantages when used with objects having a repeating pattern of features in an X-Y plane, such as a patterned array having an attached collection of molecules, such as DNA, RNA, biological material from viruses, proteins, antibodies, carbohydrates, small molecules (such as drug candidates), biologically active molecules, or any other analytes of interest.

An increasing number of applications have been developed for arrays with features having biological molecules, such as nucleic acids and polypeptides. Such patterned arrays may include DNA or RNA probes. These are specific for nucleotide sequences present in plants, animals (e.g., humans), and other organisms. In some applications, for example, individual DNA or RNA probes can be attached at individual features or sites of an array. A test sample, such as from a known or unknown person or organism, can be exposed to the array, such that target nucleic acids (e.g., gene fragments, mRNA, or amplicons thereof) hybridize to complementary probes at respective features or sites in the array. The probes can be labeled in a target specific process (e.g., due to labels present on the target nucleic acids or due to enzymatic labeling of the probes or targets that are present in hybridized form at the features). The array can then be examined, such as by scanning specific frequencies of light over the features to identify which target nucleic acids are present in the sample.

Biological patterned arrays may be used for genetic sequencing and similar applications. In general, genetic sequencing includes determining the order of nucleotides in a length of target nucleic acid, such as a fragment of DNA or RNA. Relatively short sequences may be sequenced at each feature, and the resulting sequence information may be used in various bioinformatics methods to logically fit the sequence fragments together, so as to reliably determine the sequence of much more extensive lengths of genetic material from which the fragments are available. Automated, computer-based algorithms for characterizing fragments have been developed, and have been used more recently in genome mapping, identification of genes and their function, and so forth. Patterned arrays are useful for characterizing genomic content because a large number of variants are present and this supplants the alternative of performing many experiments on individual probes and targets. The patterned array may be a desirable format for performing such investigations in a practical manner.

As noted above, any of a variety of analyte arrays (also referred to in the present disclosure as "patterned arrays" or simply as "arrays") known in the art can be used in a method or system set forth herein. Such arrays contain features, each having an individual probe or a population of probes. In the latter case, the population of probes at each feature may be homogenous having a single species of probe. For example, in the case of a nucleic acid array, each feature can have multiple nucleic acid molecules each having a common sequence. However, in some other examples, the populations at each feature of an array can be heterogeneous. Similarly, protein arrays can have features with a single protein or a population of proteins, which may or may not have the same amino acid sequence. The probes can be attached to the surface of an array, for example, via covalent linkage of the probes to the surface or via non-covalent interaction of the probes with the surface. In some examples, probes, such as nucleic acid molecules, can be attached to a surface via a gel layer as described, for example, in U.S. Pat. No. 9,012,022 and U.S. Pat. App. Pub. No. 2011/0059865 A1, each of which is incorporated herein by reference in its entirety.

Example arrays include, without limitation, a Bead-Chip™ Array available from Illumina, Inc., or others including those where probes are attached to beads that are present on a surface (e.g., beads in wells on a surface) such as those described in U.S. Pat. Nos. 6,266,459; 6,355,431; 6,770,441; 6,859,570; or 7,622,294; or PCT Pub. No. WO 00/63437, each of which is incorporated herein by reference in its entirety. Further examples of commercially available patterned arrays that can be used include, for example, GeneChip® available from Affymetrix (part of Thermo Fisher Scientific). Patterned arrays, or other patterned arrays synthesized in accordance with techniques sometimes referred to as VLSIPS™ (Very Large Scale Immobilized Polymer Synthesis) technologies, available from VLSIP Technologies. A spotted patterned array can also be used in a method or system according to some examples of the present disclosure. An example spotted patterned array is a CodeLink™ array available from Amersham Biosciences. Another patterned array that may be useful is one that is manufactured using inkjet printing methods such as Sure-Print™ Technology available from Agilent Technologies.

Other useful arrays include those that are used in nucleic acid sequencing applications. For example, arrays having amplicons of genomic fragments (often referred to as clusters) are useful such as those described in Bentley et al., Nature 456:53-59 (2008), WO 04/018497; WO 91/06678; WO 07/123744; U.S. Pat. Nos. 7,329,492; 7,211,414; 7,315,019; 7,405,281, or 7,057,026; or U.S. Pat. App. Pub. No. 2008/0108082 A1, each of which is incorporated herein by reference in its entirety. Another type of array that is useful for nucleic acid sequencing is an array of particles produced from an emulsion PCR technique. Examples are described in Dressman et al., Proc. Natl. Acad. Sci. USA 100:8817-8822 (2003), WO 05/010145, U.S. Pat. App. Pub. No. 2005/0130173 or U.S. Pat. App. Pub. No. 2005/0064460, each of which is incorporated herein by reference in its entirety.

Arrays used for nucleic acid sequencing often have random spatial patterns of nucleic acid features. For example, HiSeq™ or MiSeq™ sequencing platforms available from Illumina Inc. utilize flow cells comprising supports or arrays upon which nucleic acid(s) is/are disposed by random seeding followed by bridge amplification. However, patterned arrays can also be used for nucleic acid sequencing or other analytical applications. Example patterned arrays, methods for their manufacture and methods for their use are set forth in U.S. Pat. Nos. 9,512,422; 8,895,249; and 9,012,022; and in U.S. Pat. App. Pub. Nos. 2013/0116153 A1; and 2012/0316086 A1, each of which is incorporated herein by reference in its entirety. The features of such patterned arrays can be used to capture a single nucleic acid template molecule to seed subsequent formation of a homogenous colony, for example, via bridge amplification. Such patterned arrays are useful for nucleic acid sequencing applications.

The size of features, such as sites on an array (or another object used in a method or system herein), can be selected to suit a desired application. In some examples, a feature of an array can have a size that accommodates only a single nucleic acid molecule. A surface having a plurality of features in this size range is useful for constructing an array of molecules for detection at single molecule resolution. Features in this size range are also useful in arrays having features that each contain a colony of nucleic acid molecules. Thus, the features of an array can each have an area that is no larger than about 1 mm$^2$, no larger than about 500 µm$^2$, no larger than about 100 µm$^2$, no larger than about 10 µm$^2$, no larger than about 1 µm$^2$, no larger than about 500 nm$^2$, or no larger than about 100 nm$^2$, no larger than about 10 nm$^2$, no larger than about 5 nm$^2$, or no larger than about 1 nm$^2$. Alternatively or additionally, the features of an array will be no smaller than about 1 mm$^2$, no smaller than about 500 µm$^2$, no smaller than about 100 µm$^2$, no smaller than about 10 µm$^2$, no smaller than about 1 µm$^2$, no smaller than about 500 nm$^2$, no smaller than about 100 nm$^2$, no smaller than about 10 nm$^2$, no smaller than about 5 nm$^2$, or no smaller than about 1 nm$^2$. Indeed, a feature can have a size that is in a range between an upper and lower limit selected from those exemplified above. Although several size ranges for features of a surface have been exemplified with respect to nucleic acids and on the scale of nucleic acids, it will be understood that features in these size ranges can be used for applications that do not include nucleic acids. It will be further understood that the size of the features need not necessarily be confined to a scale used for nucleic acid applications.

For examples that include an object (e.g., an array or support) having a plurality of features or sites, the features can be discrete, being separated with spaces between each other. An array useful in the present techniques can have features that are separated by edge to edge distance of at most about 100 µm, about 50 µm, about 10 µm, about 5 µm, about 1 µm, about 0.5 µm, or less. Alternatively or additionally, an array can have features that are separated by an edge to edge distance of at least about 0.5 µm, about 1 µm, about 5 µm, about 10 µm, about 50 µm, about 100 µm, or more. These ranges can apply to the average edge to edge spacing for features, as well as to the minimum or maximum spacing.

In some examples the features of an array need not be discrete, and instead, neighboring features can abut each other. Whether or not the features are discrete, the size of the features and/or pitch of the features can vary such that arrays can have a desired density. For example, the average feature pitch in a regular pattern can be at most about 100 µm, about 50 µm, about 10 µm, about 5 µm, about 1 µm, or about 0.5 µm or less. Alternatively or additionally, the average feature pitch in a regular pattern can be at least about 0.5 µm, about 1 µm, about 5 µm, about 10 µm, about 50 µm, or about 100 µm or more. These ranges can apply to the maximum or minimum pitch for a regular pattern as well. For example, the maximum feature pitch for a regular pattern can be at most about 100 µm, about 50 µm, about 10 µm, about 5 µm, about 1 µm, or about 0.5 µm or less; and/or the minimum feature pitch in a regular pattern can be at least about 0.5 µm, about 1 µm, about 5 µm, about 10 µm, about 50 µm, or about 100 µm or more.

The density of features in an array can also be understood in terms of the number of features present per unit area. For example, the average density of features for an array can be at least about $1\times10^3$ features/mm$^2$, about $1\times10^4$ features/mm$^2$, about $1\times10^5$ features/mm$^2$, about $1\times10^6$ features/mm$^2$, about $1\times10^7$ features/mm$^2$, about $1\times10^8$ features/mm$^2$, or about $1\times10^9$ features/mm$^2$ or higher. Alternatively or additionally, the average density of features for an array can be at most about $1\times10^9$ features/mm$^2$, about $1\times10^8$ features/mm$^2$, about $1\times10^7$ features/mm$^2$, about $1\times10^6$ features/mm$^2$, about $1\times10^5$ features/mm$^2$, about $1\times10^4$ features/mm$^2$, or about $1\times10^3$ features/mm$^2$ or less.

The features in a patterned example can have any of a variety of pattern shapes and layouts. For example, when observed in a two dimensional plane, such as on the surface of an array, the features can appear rounded, circular, oval, rectangular, square, symmetric, asymmetric, triangular, polygonal, or the like. The features can be arranged in a regular repeating pattern including, for example, a hexagonal or rectilinear pattern. A pattern can be selected to achieve a desired level of packing. For example, round features are optimally packed in a hexagonal arrangement. Of course other packing arrangements can also be used for round features and vice versa.

In general, a pattern might be characterized in terms of the number of features that are present in a subset that forms the smallest geometric unit of the pattern. The subset can include, for example, at least 2, 3, 4, 5, 6, 10 or more features. Depending upon the size and density of the features, the geometric unit can occupy an area of less than about 1 mm$^2$, about 500 µm$^2$, about 100 µm$^2$, about 50 µm$^2$, about 10 µm$^2$, about 1 µm$^2$, about 500 nm$^2$, about 100 nm$^2$, about 50 nm$^2$, or about 10 nm$^2$ or less. Alternatively or additionally, the geometric unit can occupy an area of greater than about 10 nm$^2$, about 50 nm$^2$, about 100 nm$^2$, about 500 nm$^2$, about 1 µm$^2$, about 10 µm$^2$, about 50 µm$^2$, about 100 µm$^2$, about 500 µm$^2$, or about 1 mm$^2$ or more. Characteristics of the features in a geometric unit, such as shape, size, pitch and the like, can be selected from those set forth herein more generally with regard to features in an array or pattern.

An array having a regular pattern of features can be ordered with respect to the relative locations of the features but random with respect to one or more other characteristic of each feature. For example, in the case of a nucleic acid array, the nucleic acid features can be ordered with respect to their relative locations but random with respect to one's knowledge of the sequence for the nucleic acid species present at any feature. As a more specific example, nucleic acid arrays formed by seeding a repeating pattern of features with template nucleic acids and amplifying the template at each feature to form copies of the template at the feature (e.g., via cluster amplification or bridge amplification) will have a regular pattern of nucleic acid features but will be random with regard to the distribution of sequences of the nucleic acids across the array. Thus, detection of the presence of nucleic acid material on the array can yield a repeating pattern of features, whereas sequence specific detection can yield non-repeating distribution of signals across the array.

It will be understood that the description herein of patterns, order, randomness and the like pertain not only to features on objects, such as features on arrays, but also to features in image data or, where produced, in actual images. As such, patterns, order, randomness and the like can be present in any of a variety of formats that are used to store, manipulate or communicate image data including, but not limited to, a computer readable medium or computer component such as a graphical user interface or other output device.

Fiducials are included on or in the arrays contemplated in the present disclosure, such as on one or more surfaces of patterned array supports or substrates (whether in an array or in any random or other layout), as well as in image data of the sites and molecules to facilitate identification and localization of individual features on the array, including the sites at which the molecules are located. Fiducials are useful for registering the spatial locations of sites or features since the fiducials provide a point of reference for relative locations of such sites or features. Fiducials are especially beneficial for applications where a support and sites are detected repeatedly to follow changes occurring at individual sites over time and successive cycles of processing. For example, fiducials can allow individual nucleic acid clusters to be followed through successive images obtained over multiple sequencing cycles, such that the sequence of nucleic acid species present at individual clusters can be accurately determined.

Turning now to the drawings, and referring first to FIG. 1, an example analysis system 10 is illustrated for processing patterned arrays (such as for biological applications), imaging the patterned arrays, and analysis of data derived from the imaging. In the illustrated example, the system 10 is designed to introduce molecules, such as nucleotides, oligonucleotides, and other bioactive reagents, into samples (S) 12 that may be prepared in advance. The system 10 may be designed for synthesizing biopolymers, such as DNA chains, or for sequencing biopolymers. It is noted that the present technique is not limited in any way to sequencing operations, gene expression operations, diagnostic applications, or any one of these, but may be used in any of them for analyzing collected image data for multiple swaths or regions detected in regions of a sample as described below. Other substrates containing arrays of molecules or other detectable features can similarly be used in the techniques and systems disclosed.

In the illustrated example, however, example biopolymers might include, nucleic acids, such as DNA, RNA, or analogs of DNA or RNA. Other example biopolymers might include proteins (also referred to as polypeptides), polysaccharides, or analogs thereof. Although any of a variety of biopolymers may be used, for the sake of clarity, the systems and methods used for processing and imaging in the example context illustrated in FIG. 1 will be described with regard to the processing of nucleic acids. In general, the system illustrated in FIG. 1 will act upon samples 12 which may include an array of reaction sites. Here again, as used herein, the term "array" or "patterned array" refers to a support having a population of different reaction sites on one or more substrates, such that different reaction sites can be differentiated from each other according to their relative location. A single species of biopolymer may be attached to each individual reaction site. However, multiple copies of a species of biopolymer can be attached to a reaction site. The array, taken as a whole, may include a plurality of different biopolymers attached at a plurality of different sites. Reaction sites can be located at different addressable locations on the same substrate. Alternatively, an array can include separate substrates, such as beads, each forming a different reaction site. The sites may include fragments of DNA attached at specific locations in an array, or may be wells in which a target product is to be synthesized. In some applications, the system may be designed for continuously synthesizing or sequencing molecules, such as polymeric molecules based upon common nucleotides.

In the diagrammatical representation of FIG. 1, analysis system 10 may include a processing system 14 designed to process samples 12, such as biological patterned arrays, and to generate image data representative of individual sites on the patterned array, as well as spaces between sites, and representations of fiducials provided in or on the patterned array support. A data analysis system 16 receives the image data and processes the image data in accordance with the present disclosure, to extract meaningful values from the imaging data as described below. A downstream processing/storage system 18, then, may receive this information and store the information, along with imaging data, where desired. The downstream processing/storage system 18 may further analyze the image data or the data derived from the image data, such as to diagnose physiological conditions, compile sequencing lists, analyze gene expression, and so forth.

The processing system 14 may employ a biomolecule reagent delivery system 20 (shown as a nucleotide delivery system in FIG. 1) for delivering various reagents to a sample 12 as processing progresses. System 14 may include a plurality of operations through which samples 12 and sample containers progress. This progression can be achieved in a number of ways including, for example, physical movement of the sample 12 to different stations, or loading of the array in a system in which the array is moved or an optical system is moved, or both, or the delivery of fluids is performed via valve actuation. A system may be designed for cyclic operation in which reactions are promoted with single nucleotides or with oligonucleotides, followed by flushing, imaging and de-blocking in preparation for a subsequent cycle. In a practical system, the samples 12 are disposed in the system and an automated or semi-automated sequence of operations is performed for reactions, flushing, imaging, de-blocking, and so forth, in a number of successive cycles before all useful information is extracted from the test sample. Again, it should be noted that the process illustrated in FIG. 1 is by no means limiting, and the present techniques may operate on image data acquired from any suitable system employed for any application. It should be noted that while reference is made in the present disclosure to "imaging" or "image data", in many practical systems this will entail actual optical imaging and extraction of data from electronic detection circuits (e.g., cameras or imaging electronic circuits or chips), although other detection techniques may also be employed, and the resulting detected data characterizing the molecules of interest should also be considered as "images" or "image data".

In the example illustrated in FIG. 1, the nucleotide delivery system 20 provides a process stream 22 to the samples 12. An effluent stream 24 from the array or flow cell may be recaptured and recirculated, for example, in the nucleotide delivery system 20. In the illustrated example, then, the array or flow cell may be flushed at a flush station 26 (or in many cases by flushing by actuation of appropriate valving) to remove additional reagents and to clarify the sample 12 for imaging. The sample 12 is then exposed to an imaging system 28 (which may be within the same device) where image data may be generated that can be analyzed, for example, for determination of the sequence of a progressively building nucleotide chain, such as based upon a template. In a presently contemplated example, the imaging system 28 may employ confocal line scanning to produce progressive pixilated image data that can be analyzed to locate individual sites in an array and to determine the type of nucleotide that was most recently attached or bound to each site. Other imaging techniques may also suitably be employed, such as techniques in which one or more points of radiation are scanned along the sample, or techniques employing "step and shoot" imaging approaches.

As noted, the imaging components of the system 28 may be more generally considered a "detection apparatus", and any detection apparatus that is capable of high resolution imaging of surfaces may be useful. In some examples, the detection apparatus will have sufficient resolution to distinguish features at the densities, pitches and/or feature sizes set forth herein. Examples of the detection apparatus are those that are configured to maintain an object and detector in a static relationship while obtaining an area image. As noted, a scanning apparatus can be used, as well as systems that obtain successive area images (e.g. "step and shoot" detectors). Point scanning detectors mentioned above can be configured to scan a point (i.e., a small detection area) over the surface of an object via a raster motion in the X-Y plane of the surface. Line scanning detectors can be configured to scan a line along the Y dimension of the surface of an object, where the longest dimension of the line occurs along the X dimension. It will be understood that the detection device, object or both can be moved to achieve scanning detection. Detection apparatuses that are useful, for example in nucleic acid sequencing applications, are described in U.S. Pat. App. Pub. Nos. 2012/0270305 A1; 2013/0023422 A1; and 2013/0260372 A1; and U.S. Pat. Nos. 5,528,050; 5,719,391; 8,158,926 and 8,241,573, all of which are incorporated herein by reference in their entirety.

Following imaging (e.g., at imaging system 28), then, the samples 12 may progress to a deblock station 30 for de-blocking, during which a blocking molecule or protecting group is cleaved from the last added nucleotide, along with a marking dye. If the system 14 is used for sequencing, by way of example, image data from the imaging system 28 will be stored and forwarded to a data analysis system as indicated at reference numeral 16.

The analysis system 16 may include a general purpose or application-specific programmed computer, which provides a user interface and automated or semi-automated analysis of the image data to determine which of the four common DNA nucleotides may have been last added at each of the sites in an array of each sample, as described below. As will be appreciated by those skilled in the art, such analysis may be performed based upon the color of unique tagging dyes for each of the four common DNA nucleotides. This image data may be further analyzed by the downstream processing/storage system 18, which may store data derived from the image data as described below, as well as the image data itself, where appropriate. Again, the sequencing application is intended to be one example, and other operations, such as diagnostic applications, clinical applications, gene expression experiments, and so forth may be carried out that will generate similar imaging data operated on by the present techniques.

As noted above, in some implementations, the patterned array may remain in a fixed position, and the "stations"

referred to may include integrated subsystems that act on the patterned array as described (e.g., for introduction and reaction with desired chemistries, flushing, imaging, image data collection, and so forth). The data analysis may, here again, be performed contemporaneously with the other processing operations, or may be done post-processing by accessing the image data, or data derived from the image data, from an appropriate memory (in the same system, or elsewhere). In many applications, a patterned array "container" will comprise a cartridge in which the patterned array is placed and through which the desired chemistry is circulated. In such applications, imaging may be done through and via the flow cell. The flow cell may be appropriately located (e.g., in the X-Y plane), and moved (e.g., in X, Y, and Z directions) as needed for imaging. Connections for the desired chemistry may be made directly to the flow cell when it is mounted in the apparatus. Moreover, depending upon the device design and the imaging technique used, the patterned array, encased in the flow cell, may be initially located in the X-Y plane, and moved in this plane during imaging, or imaging components may be moved parallel to this plane during imaging. In general, here again, the "X-Y plane" is the plane of the patterned array surface that supports the sites, or a plane parallel to this. The flow cell, therefore, may be said to extend in the X-Y plane, with the X direction being the longer direction of the flow cell, and the Y direction being the shorter direction (the flow cells being rectangular). It is to be understood, however, that this orientation could be reversed. The flow cell and patterned array may also be moved in the Z direction, which is the direction orthogonal to both the X and Y directions. Such movements may be useful for securing the flow cell into place, for making fluid connections to the flow cell, and for imaging (e.g., focusing the optic for imaging sites at precise Z depths). In some applications, the optic may be moved in the X direction for precise imaging.

Figure 2:
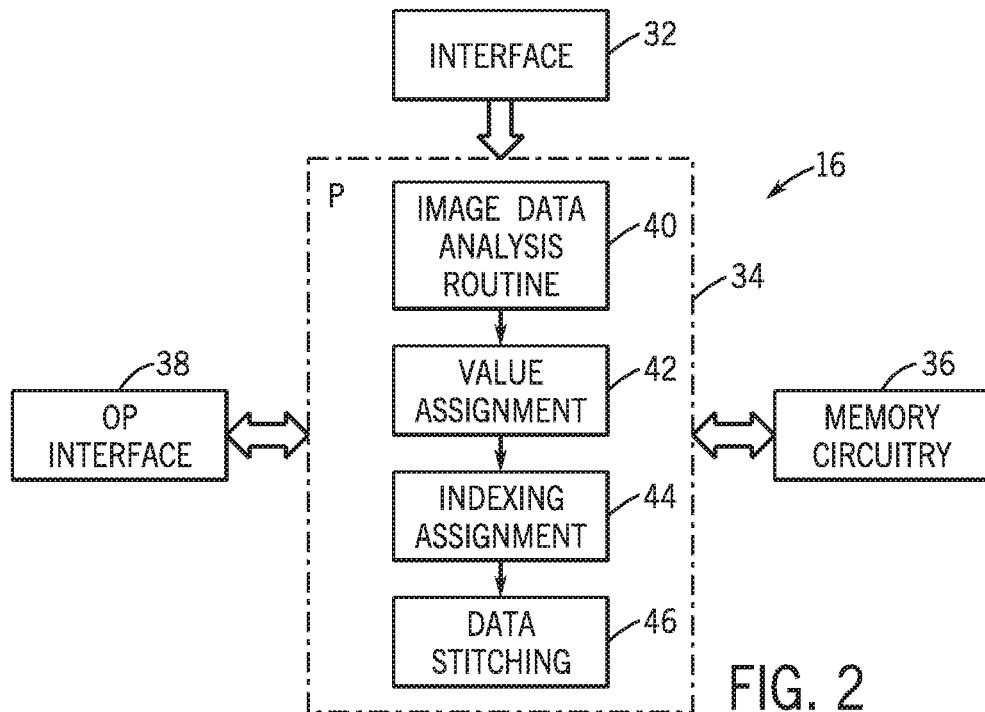
FIG. 2 is a diagrammatical overview of the functional components that may be included in a data analysis system for use in a system of the type illustrated in FIG. 1.

FIG. 2 illustrates an example data analysis system 16 and some of its functional components insomuch as they relate to the present techniques. As noted above, the system 16 may include one or more programmed computers, with programming being stored on one or more machine readable media with code executed to carry out the processes described. In the illustrated example, the system 16 includes an interface 32 designed to permit networking of the system 16 to one or more imaging systems 28 acquiring image data of patterned arrays. The interface may receive and condition data, where appropriate. In general, however, the imaging system 28 will output digital image data representative of individual picture elements or pixels that, together, form an image of the patterned array (or a portion of it). A processor, denoted by reference numeral 34 in FIG. 2, processes the received image data in accordance with a plurality of routines defined by processing code. The processing code may be stored in various types of memory circuitry, as represented by reference numeral 36 in FIG. 2. As used in this disclosure, the term "machine readable" means detectable and interpretable by a machine, such as a computer, processor, or a computer or processor in cooperation with detection and signal interpretation devices or circuits (e.g., computer memory and memory access components and circuits, imaging or other detection apparatus in cooperation with image or signal interpretation and processing components and circuits), and so forth.

Computers and processors useful for the present techniques may include specialized circuitry and/or general purpose computing devices, such as a processor that is part of a detection device, networked with a detection device used to obtain the data that is processed by the computer, or separate from the detection device. In some examples, information (e.g., image data) may be transmitted between components of a system 16 disclosed herein directly or via a computer network. A Local Area Network (LAN) or Wide Area Network (WAN) may be a corporate computing network, including access to the Internet, to which computers and computing devices comprising the system 16 are connected. In one example, the LAN conforms to the Transmission Control Protocol/Internet Protocol (TCP/IP) industry standard. In some instances, the information (e.g., image data) is input to a system 16 disclosed herein via an input device (e.g., disk drive, compact disk player, USB port, etc.). In some instances, the information is received by loading the information, such as from a storage device such as a disk or flash drive.

As noted above, in some examples, the processing circuitry may process image data in real or near-real time while one or more sets of image data of the support, sites, molecules, etc. are being obtained. Such real time analysis is useful for nucleic acid sequencing applications wherein an array of nucleic acids is subjected to repeated cycles of fluidic and detection operations. Analysis of the sequencing data can often be computationally intensive such that it can be beneficial to perform the methods in real or near-real time or in the background while other data acquisition or analysis algorithms are in process. Example real time analysis methods that can be used with the present methods are those used for the MiSeq™ and HiSeq™ sequencing devices commercially available from Illumina, Inc. and/or described in U.S. Pat. App. Pub. No. 2012/0020537 A1, which is incorporated herein by reference in its entirety. The terms "real time" and "near-real time", when used in conjunction with the processing of samples and their imaging are intended to imply that the processing occurs at least in part during the time the samples are being processed and imaged. In other examples, image data may be obtained and stored for subsequent analysis by similar algorithms. This may permit other equipment (e.g., powerful processing systems) to handle the processing tasks at the same or a different physical site from where imaging is performed. This may also allow for re-processing, quality verification, and so forth.

In accordance with the presently contemplated examples of techniques, the processing code executed on the image data includes an image data analysis routine 40 designed to analyze the image data. Image data analysis may be used to determine the locations of individual sites visible or encoded in the image data, as well as locations in which no site is visible (i.e., where there is no site, or where no meaningful radiation was detected from an existing site). Image data analysis may also be used to determine locations of fiducials that aid in locating the sites. Still further, image data analysis may be used for locating the patterned array in the system, for providing useful information for processing or reference purposes, and so forth.

As will be appreciated by those skilled in the art, in a biological patterned array imaging setting, locations in the patterned array, either laid out in a grid pattern or randomly, will appear brighter than non-site locations due to the presence of fluorescing dyes attached to the imaged molecules. It will be understood that the sites need not appear brighter than their surrounding area for example when a target for the probe at the site is not present in a sample being detected. The color at which individual sites appear may be a function of the dye employed, as well as of the wavelength of the light used by the imaging system 28 for imaging purposes. Sites to which targets are not bound or that are otherwise devoid of a label can be identified according to other characteristics, such as their expected location in the patterned array. Any fiducial markers may appear on one or more of the images, depending upon the design and function of the markers.

Once the image data analysis routine 40 has located individual sites in the image data, a value assignment may be carried out as indicated at reference numeral 42, often as a function of, or by reference to any fiducial markers provided. In general, the value assignment carried out at 42 will assign a digital value to each site based upon characteristics of the image data represented by pixels at the corresponding location. That is, for example, the value assignment routine 42 may be designed to recognize that a specific color or wavelength of light was detected at a specific location, as indicated by a group or cluster of pixels at the location. In a DNA imaging application, for example, the four common nucleotides may be represented by separate and distinguishable colors (or more generally, wavelengths or wavelength ranges of light). Each color, then, may be assigned a value corresponding to that nucleotide. The value assignment carried out by routine 42, then, will assign the corresponding value to the entire site, alleviating the need to further process the image data itself, which will be much more voluminous (e.g., many pixels may correspond to each site) and of significantly larger numerical values (i.e., much larger number of bits to encode each pixel).

An indexing assignment routine 44, then, will associate each of the assigned values with a location in an image index or map, which, again, may be made by reference to known or detected locations of fiducial markers, or to any data encoded by such markers. As described more fully below, the map will correspond to the known or determined locations of individual sites within the sample 12. A data analysis algorithm 46 (shown as data stitching 46 in FIG. 2), which may be provided in the same or a different physical device, allows for identification or characterization of the molecules of the sample 12, as well as for logical analysis of the molecular data, where desired. For sequencing, for example, the algorithm may permit characterization of the molecules at each site by reference to the emission spectrum (that is, whether the site is detectable in an image, indicating that a tag or other mechanism produced a detectable signal when excited by a wavelength of light). The molecules at the sites, and subsequent molecules detected at the same sites may then be assembled logically into sequences. These short sequences may then be further analyzed by the algorithm 46 to determine probable longer sequences in which they may occur in the sample donor subject.

It may be noted that as in the illustration of FIG. 2, an operator (OP) interface 38 may be provided, which may consist of a device-specific interface, or in some applications, to a conventional computer monitor, keyboard, mouse, and so forth to interact with the routines executed by the processor 34. The operator interface 38 may be used to control, visualize or otherwise interact with the routines as imaging data is processed, analyzed and resulting values are indexed and processed.

Figure 3:
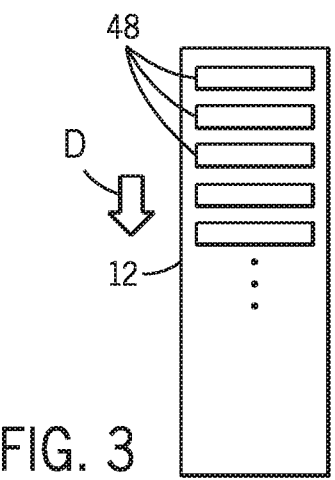
FIG. 3 is a plan view of an example biological patterned array of the type that may be used in conjunction with the present techniques.

FIG. 3 illustrates an example sample or patterned array 12. As shown in FIG. 3, a plurality of grids or swaths 48 may be provided such that each will include a multitude of individual sites to be imaged. As noted above, a wide range of layouts for such patterned arrays are possible, and the present techniques are not intended to be limited to any desired or particular layout. In a progressively scanning example, as imaging progresses, the sample or patterned array 12 will be moved in an indexed direction D so that each of the grids 48 can be imaged. Initial fiducial markers (not shown), sometimes referred to as "coarse alignment" or "auto-centering" fiducials may be formed in or on the support, such as to allow for properly locating the grids or swaths 48, or for locating the patterned array in a processing system 14 or imaging system 28. It should be noted that in the view of FIG. 3, the surrounding flow cell in which the patterned array may be located is not shown.

Figure 4:
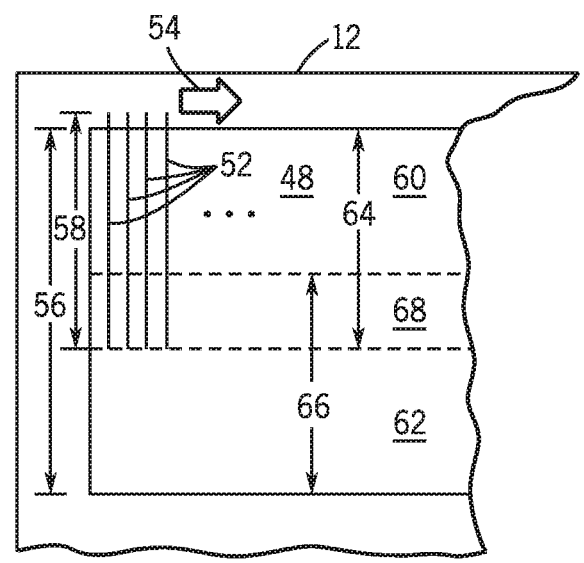
FIG. 4 is an enlarged, cut-away view of a portion of the patterned array of FIG. 3.

FIG. 4 is an enlarged illustration of one of the swaths 48 of the patterned array of FIG. 3. As shown in FIG. 4, depending upon the imaging technique employed, the swath 48 may be scanned by the imaging system 28 in parallel scan lines 52 that progressively move along the swath 48. In practice, a point may be scanned over a region of the swath 48 corresponding to each of lines 52. Moreover, in many systems the patterned array will be moved slowly in one direction, as indicated by arrow 54, while the imaging optic will remain stationary. The parallel scan lines 52 will then result from the progressive movement of the sample. Though not shown in FIG. 4, each swath 48 may include regions designated as fiducial markers that can be similarly imaged and identified in resulting image data.

In the illustrated example, the grid or swath 48 of the patterned array has a width 56 which may be wider than the length 58 of the scan lines 52 of which the imaging system 28 is capable of generating or imaging in each pass. That is, the entire width 56 may not be scanned or imaged in a single pass. This may be due to the inherent limitation of the line length 58 due to the imaging optics, limitations relating to focusing or movement of components, such as mirrors or other optical components used to generate the scan lines, limitations in digital detectors, and so forth. The swath 48 may be scanned in multiple passes, and values for each of the sites may be extracted from the image data as mentioned above.

In FIG. 4, for example, the overall width 56 of the swath 48 can be accommodated in two overlapping areas 60 and 62. The width of each area 60 and 62, as indicated by reference numerals 64 and 66, respectively, will be slightly less than the length 58 of the scan lines 52. This will permit detection of a feature used to integrate the values derived from the image data, such as by reference to an edge or other feature. It may be noted that a common area or overlap 68 exists that may be imaged in both passes.

Figure 5:
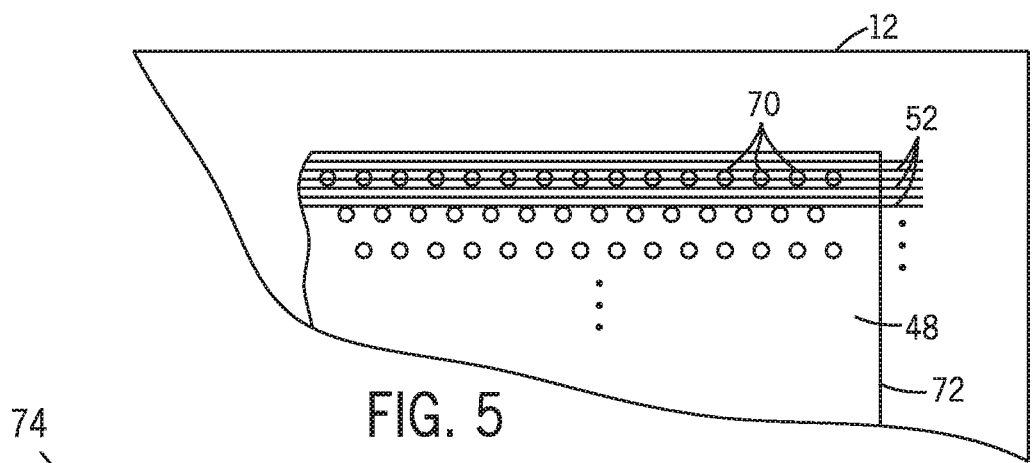
FIG. 5 is a further cut-away diagram illustrating sites on an example array.

FIG. 5 illustrates, in somewhat greater detail, scan lines 52 over a plurality of sites 70 in the swath 48 illustrated in FIG. 4. As noted above, in some implementations, the sites 70 may be laid out in any suitable grid pattern, or even randomly. In the illustrated example, the sites 70 are laid out in a hexagonal pattern, although rectangular patterns, and other patterns may be employed. The location of each site 70 will be known with reference to one or more fiducial features, such as an edge 72 of the grid or portion of the patterned array. In the case of random site locations, these may be located and mapped by an initial imaging sequence designed to detect the location of all sites of interest.

Figure 6:
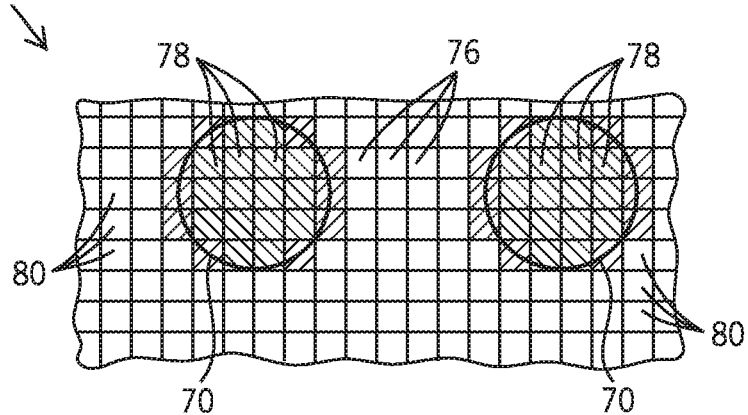
FIG. 6 is an enlarged view of two example sites illustrating pixilation in image data for the sites during processing.

FIG. 6 represents a portion of an example image of the type that will be generated based upon image data collected by progressive scanning of the region of interest in the patterned array. The actual image 74 is composed of a large number of pixels 76 each of which corresponds to a digital value from the imaging system 28. The pixel data, which represents the image 74, will encode values corresponding to bright pixels 78 and darker pixels 80. In practice, various grey levels or even color encoding can be employed such that the individual sites 70 can be identified by detecting contrast between the pixels as indicated by their individual digital values.

Before discussing some presently contemplated forms, types, and uses of fiducials, a brief discussion is provided here of example algorithms or processing for the use, data encoding and decoding, and registration of site and image data based on the fiducial techniques disclosed. Registration of fiducials, and thereby of sites 70, detectible in image data of sequential imaging operations can be carried out by lining up (e.g., locating and overlaying) the fiducials, determining the two dimensional cross-correlation (or other measure of the similarity of fit), for example, based on the number of bright pixels 78 from the image data, and determining the offset between the fiducials. The offset can be determined, for example, via an iterative process whereby the following operations are repeated: one of the fiducials is shifted relative to the other, the change in level of correlation of fit is determined (e.g., an increase in correlation being indicated by an increase in the number of bright pixels 78 of fiducials that overlap), and a determined location of one or more of the fiducials is shifted in a direction that increases the correlation of fit. Iterations can proceed until an offset that produces an optimal or otherwise desired correlation is determined. A transform can be determined based on the offset and the transform can be applied to the rest of the features in the target image. Thus, the locations for the features in a target image can be determined by shifting the relative scale and/or orientation between the image data, using a transform based on an offset determined between fiducials in the image data when overlaid.

Any of a variety of transform models can be used. Global transforms are useful including, for example, linear transforms or affine transforms. The transformations can include, for example, one or more of rotation, translation, scaling, shear, or the like. An elastic or non-rigid transform can also be useful, for example, to adjust for distortions in target detection data or reference data. Distortions can arise when using a detection apparatus that scans a line along they dimension of an object, where the longest dimension of the line occurs along the X dimension. For example, stretching distortions can occur along the X dimension (and sometimes only along X). Distortions can arise for other detectors including, for example, spreading distortions in both X and Y resulting from an area detector. An elastic or non-rigid transform can be used to correct for distortions, such as linear distortions present in image data obtained from line scanning instruments, or spreading distortions present in image data obtained from area detectors. Alternatively or additionally, a correction factor can be applied to the reference data, target data and/or the transform to correct distortions introduced (or expected to be introduced) by a detection apparatus. For examples where patterned features are imaged, a non-linear correction can be applied to feature locations as a function of X position. For example, the non-linear correction that is applied can be a third order polynomial to account for distortion arising from the optical system that was used for detection of the features.

Thus, by analyzing the image data to identify and locate the fiducials, reference data can contain information about the position of a fiducial in an X-Y plane. Alternatively or additionally, reference data can include information about the position of the same or other fiducials in the Z dimension. In the case of imaging data, focus can be altered by translation along the Z dimension. As such, an algorithm can be used to determine focus for the features of an object based on comparison of a fiducial in a reference data set to a fiducial in the data from a target image.

In some examples, reference data can be obtained from empirical detection of an object. For example, an object can be detected under known conditions and the resulting data set used for registration of subsequent data acquired from the same object (albeit under different conditions). Alternatively, a model, standard or template object can be empirically detected to create reference data. This reference data can be used for registration of a similar object. In other examples, reference data can be obtained from a theoretical object, such as a design, blueprint or manufacturing specification for an object that is to be subsequently detected.

In some examples, registration information can be communicated to a user via a graphical user interface (GUI). However, examples of the methods set forth herein can be carried out in an automated fashion that does not necessarily call for human intervention. Accordingly, in some examples, registration information (e.g., overlaid images of fiducials) is not communicated to a user, whether via a GUI or other format.

The methods and systems described can be used for an array of nucleic acids that has been subjected to any of a variety of nucleic acid sequencing techniques. Applicable techniques may include those wherein nucleic acids are attached at features of an array such that their relative positions do not change, and wherein the array is repeatedly detected (e.g., using optical imaging) through multiple sequencing cycles. Examples in which images are obtained in different color channels, for example, coinciding with different labels used to distinguish one nucleotide base type from another, are applicable. In some examples, the process to determine the nucleotide sequence of a target nucleic acid can be an automated process. Examples may include sequencing-by-synthesis ("SBS") techniques, available from Illumina, Inc.

Nucleic acids can be sequenced by providing different nucleotides (or oligonucleotides) to an array of features so as to produce different signals at each feature, each signal corresponding to a specific species of nucleotide (or oligonucleotide) that has been added to the feature. For example, in the case mentioned above where four different labels are used, corresponding to four different species of nucleotide (or oligonucleotide), individual images can be acquired, wherein each image captures a single color (or other signal type) among the four possible colors (or signal types). In this example, the signal color is different for each of the four different images, thereby producing a cycle of four color images that corresponds to the four possible nucleotides present at a position in the nucleic acid. Such methods can further include providing additional labeled nucleotides (or oligonucleotides) to the array of molecules, thereby producing a plurality of cycles of color images. Some example sequencing techniques that produce images from multiple cycles, and often multiple images per cycle, are set forth below in further detail.

It should be noted that a number of different imaging technologies, light wavelengths, and processing techniques may be used while employing the fiducial marker techniques disclosed. For example, some systems may use four different wavelengths or wavelength ranges. These will depend upon the excitation and emission spectra of the tags or markers used for the molecules of interest on the support. For example, such wavelengths may include about 532 nm, about 630 nm, about 660 nm, and about 700 nm. As will be appreciated by those skilled in the art, dye sequencing may include "tagmentation" or amplification (e.g., via reduced cycle amplification, bridge amplification, clonal amplification or so-called sequence by synthesis (SBS)), and the wavelengths used for imaging of sites (and molecules of interest) will be adapted for the processing used. In some techniques, for example, two-color sequencing chemistry may allow for distinction between nucleotides (e.g., one of two colors, no color, or both colors). In the latter techniques, light sources used for imaging may employ lasers having two wavelengths, such as about 532 nm and about 660 nm. Sensing circuitry may be selected to permit detection at such wavelengths for imaging, and its resolution or pixel density will allow for a sufficient number of pixels to have detectible values in the image data for detection of sites 70 at the resolution or density or the sites 70 on the support.

Regarding the detection protocols, some examples may utilize fewer detection moieties than the number of analytes targeted for detection. For example, for detecting the incorporation of four analytes (e.g., during a sequencing reaction) each of the analytes can be differentially labeled and detected by one of four excitation/emission filters (e.g., fluorescent sequencing). Alternatively, methods and systems can also be utilized wherein one dye, or a plurality of dyes with similar detection characteristics, are used when detecting and differentiating multiple different analytes. As such, the number of detection moieties utilized is less than the number of analytes being detected, which can also serve to reduce the number of imaging events needed to determine the presence of the different analytes. The use of fewer types of detection moieties can provide the advantage of simplifying the detection device needed to differentiate different types of analytes. Differentiation can be achieved instead based on differential treatment of analytes leading to their activation, inhibition, addition, removal, destruction, quenching, or enhancement at different time points that can be separately detected. Example systems and methods that utilize fewer detection moieties than the number of analytes targeted for detection are described in U.S. Pat. App. Pub. No. 2013/0079232 A1, which is incorporated herein by reference in its entirety.

Sequencing examples can utilize pyrosequencing techniques. Pyrosequencing detects the release of inorganic pyrophosphate (PPi) as nucleotides are incorporated into the nascent strand (Ronaghi et al. (1996) Analytical Biochemistry 242(1), 84-9; Ronaghi, M. (2001) Genome Res. 11(1), 3-11; Ronaghi et al. (1998) Science 281(5375), 363; U.S. Pat. Nos. 6,210,891; 6,258,568 and 6,274,320, the disclosures of which are incorporated by reference in their entirety). In pyrosequencing, released PPi can be detected by being converted to adenosine triphosphate (ATP) by ATP sulfurylase, and the level of ATP generated can be detected via luciferase-produced photons. The nucleic acids to be sequenced can be attached to a repeating pattern of features in an array and the array can be imaged to capture the chemiluminescent signals that are produced due to incorporation of nucleotides at the features of the array. An image can be obtained after the array is treated with a nucleotide type (e.g., A, T, C or G). Images obtained after addition of each nucleotide type will differ with regard to which features in the array are detected. These differences in the image reflect the different sequence content of the features on the array. However, the relative locations of each feature may remain unchanged in the images. The images can be analyzed using the systems and methods set forth herein. For example, images obtained after treatment of the array with each different nucleotide type can be handled in the same way as exemplified herein for images obtained for reversible terminator-based sequencing methods.

As mentioned above, some examples involve sequencing by ligation techniques. Such techniques utilize DNA ligase to incorporate oligonucleotides and then the incorporated oligonucleotides can be identified. The oligonucleotides may have different labels that are correlated with the identity of a nucleotide in a sequence to which the oligonucleotides hybridize. An array having a repeating pattern of features to which target nucleic acids are attached can be used and images can be obtained following treatment of the array with the labeled sequencing reagents. Each image will show nucleic acid features that have incorporated labels of a desired type. Different features will be present or absent in the different images due to the different sequence content of each feature, but the relative position of the features will remain unchanged in the images. Images obtained from ligation-based sequencing methods can be stored, processed and analyzed as set forth herein. Example sequencing by ligation systems and methods which can be utilized with the methods and systems described herein are described in U.S. Pat. Nos. 6,969,488, 6,172,218, and 6,306,597, which are incorporated herein by reference in their entirety.

More will be said about example logic for forming and utilizing the fiducials after discussing example fiducial forms, placement, and so forth below. However, as exemplified by the sequencing examples discussed above, a method of the present disclosure can include (a) providing an object having a repeating pattern of features in an X-Y plane and a fiducial; (b) obtaining a target image of the object using a detection apparatus, wherein the target image includes the repeating pattern of features and the fiducial; (c) providing data from the target image to a computer, wherein the computer has reference data, wherein the reference data includes X-Y coordinates for an imaged fiducial; (d) performing an algorithm on the computer to determine locations for the features in the target image based on comparison with the imaged fiducial; and (e) repeating operations (b), (c) and (d), wherein the algorithm determines locations for the features (e.g., sites) based upon the fiducials detected.

In the sequencing examples, different sequence content of the features (in the above method) are identified by the different wavelengths emitted from different labels and detected in the different channels of the detection apparatus.

As also exemplified by the sequencing examples, image data processed will include dark and light regions defined by image pixels. This can be the case, for example, when features are detected in a wavelength and other areas do not respond or produce a signal at that wavelength. In the sequencing example, images obtained in different wavelengths will show different subsets or groups of features that do respond to the wavelength of radiation then used.

Multiple images of patterned arrays are made at different wavelengths during processing, as discussed further below, and features responding at the different wavelengths can be detected, registered, indexed, and characterized with respect to each other, such as by using the fiducials as reference points. In images from multiple channels, for example, four images obtained for four different labels detected in a sequencing method can be combined to form a composite image once they have been registered with respect to each other. In practice, the actual images may not be produced, but image data, or a portion of the image data, or information derived from the image data (e.g., site characterization) can then be compared with images acquired at other cycles of the sequencing method. The image data acquired at these other cycles can and may comprise data from individual channels and sites, such that composite image data is compared to a single channel. Alternatively, composite image data from one cycle can be compared to composite image data from another cycle. In some examples, these comparisons include registration methods that may reference one or more of the fiducials. Thus, composite image data can be registered to a single channel image or to other composite image data.

Further, the algorithms for utilizing the fiducials, for indexing and for characterizing molecules at the sites of the patterned array will allow for determining the locations of sites, including, for example, imaging the sites and fiducials using a detection apparatus (e.g., an optical imaging system), providing data from resulting images to a computer that determines reference data including X-Y coordinates for the fiducials, and performing an algorithm on the computer to determine locations for the sites from the image data in reference to the fiducial locations. As discussed above, in general, multiple images will be made, resulting in multiple sets of image data (for each cycle of sequencing, for example, and at multiple wavelengths) that are each individually registered by reference to the fiducial locations.

Here again, in sequencing examples, the sequence of colors or wavelengths of light (or other signal characteristics) detected at each site can be used to determine the nucleotide sequence for the nucleic acid species that is present at the site. In many cases, the image data or nucleic acid species will be used to characterize respective features across a plurality of image data files to determine a property of the respective features at the sites, such as a nucleic acid sequence that is inferred from the sequence of image data (or more generally, the signals detected for the sites).

As discussed below, the fiducials may include reference marks or features that are located at least partially in the regions of the patterned array where the sites are disposed, although they may also include one or more coarse-alignment markers or features. Such markers can be used to roughly align a detection device with the patterned array. For example, in examples where the detector is an optical scanning device, the patterned array can contain one or more coarse-alignment markers that are used to roughly align the imaging optics with a location of the patterned array. In this case, the coarse-alignment markers can be positioned near the proximal edge of the patterned array, the proximal edge being at or near the initiation point for scanning of the array. Coarse-alignment markers are useful when an array is scanned in multiple swaths. In this case, the fiducials can differ along the axis that is orthogonal to the scan direction (e.g., the markers can differ along the X axis when scanning occurs along the Y axis).

In some examples, a nucleic acid array can be present on a substrate that has a pattern of strips on the proximal edge of the substrate. An optical scanner can be used to image the array in multiple swaths. The strips function as coarse-alignment markers, whereby the scanner is oriented with respect to each swath based on recognition of the pattern of the strips and movement of the imaging optics (and/or the array substrate) until the imaging optics are aligned to the desired swath. Each swath of the array will include one or more fiducials that are then used in methods set forth herein as a fine-adjust when registering images for analysis. In this way, both coarse-alignment markers and fiducials within, among, or between swaths can be used by a detection system to locate features (e.g., sites) on the array.

As exemplified above, a detection apparatus that is used in a method or system set forth herein can include a scanning detector that scans along the Y dimension of the array, wherein the scanning detector scans parallel swaths of the array. The array can further include coarse-alignment markers that distinguish the relative locations of the swaths along the X dimension. When used, the coarse-alignment markers can cooperate with the detection apparatus, such as to determine the location of at least one of the swaths. Optionally, the relative position of the detection apparatus and/or the array may be adjusted based on the location determined for the swaths. In some examples, the determining of the location of the swaths can be performed by an algorithm by a processor or computer, such as the computer that will perform registration or feature identification. Thus, the system may function to perform the algorithm on the computer to determine locations for the features in the image data, as well as to characterize molecules at each site, referenced based on the fiducials.

Regarding example implementations of the patterned arrays and flow cells in which they are disposed, flow cells having a pattern of gel-filled wells, each well occupied by a DNA colony, may be prepared as set forth in U.S. Pat. No. 9,512,422, which is incorporated herein by reference in its entirety. Briefly, a nanowell substrate may be fabricated using nanoimprint lithography to produce a hexagonal array of wells having a diameter of about 400 nm and depth of about 300 nm. The pitch of the array may be on the order of about 700 nm. A polymer (e.g., poly(N-(5-azidoacetamidylpentyl)acrylamide-co-acrylamide or "PAZAM") may be coated on the substrate and removed by polishing as described in U.S. Pat. No. 9,512,422, leaving an array of gel-filled wells. The patterned polymer substrate may then be grafted with primers as described in U.S. Pat. No. 9,012,022, which is incorporated herein by reference in its entirety. Then the wells may be seeded with phiX DNA, and clusters grown as described in U.S. Pat. No. 8,895,249, which is incorporated herein by reference in its entirety. The flow cell may be sequenced on sequencing systems available commercially from Illumina, Inc.

Regarding analysis on such systems, moreover, image data may be analyzed using the RTA protocol commercially available for Illumina sequencers. Fiducials may be formed and disposed as discussed below, such as in or partially within swaths of sites. Dark (non-signal producing regions or pixels) and light (signal producing regions or pixels) may be assigned an intensity level of 0 and 255, respectively, or any desired other level or levels between these. The data indicating the presence of a fiducial may be cross correlated at possible X-Y offsets and shifted to maximize correlation. An area may be fit, for example to a two-dimensional Gaussian to determine a subpixel X-Y shift that maximizes the cross correlation. This process can be repeated in different regions of the image where the fiducials are located. The subpixel X-Y offsets determined in each region may be used to determine an affine transform describing how features in the designed array appear on the image data.

Figure 7:
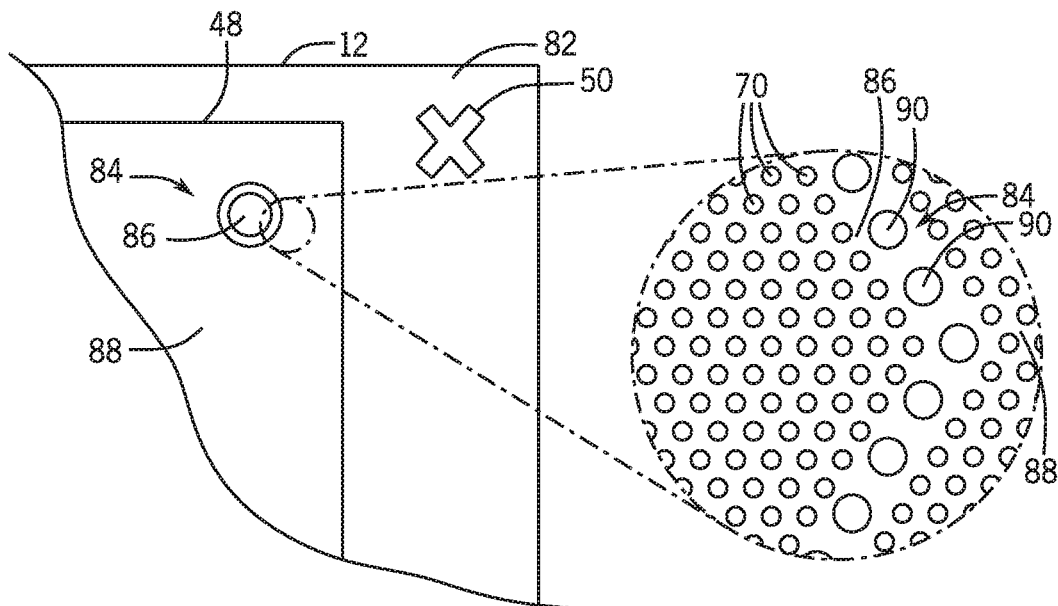
FIG. 7 is a cut-away diagrammatical representation of an example portion of a patterned array and an example fiducial formed in a site region and outside the site region.

FIGS. 7 through 22 illustrate example fiducial forms, configurations, and layouts that may be used in connection with the foregoing techniques. FIG. 7 illustrates a portion of a patterned array, in this case a corner 82. In this example, a coarse alignment or auto-centering fiducial 50 is formed near the corner 82, and may aid, as an example, in properly locating swath(s) 48. Another fiducial 84 is illustrated as being positioned within the swath 48 in which multiple sites 70 are located. Here again, the sites 70 may be formed to attach and locate molecules of interest that are imaged and characterized in a sequencing process or other process. An inner area 86 of the fiducial 84 is illustrated as including sites 70 in the inset image, while an outer area 88 comprises other sites 70. The fiducial 84 itself may be of a type that is "always on," meaning that through all phases of imaging at different wavelengths, a signal is returned by the fiducial 84.

In the illustrated example, the fiducial 84 may comprise beads 90 or other features that are disposed on or in the support of the patterned array to form a desired shape, such as a circle, closed shapes, open shapes, and so forth as discussed below.

Figure 8A:
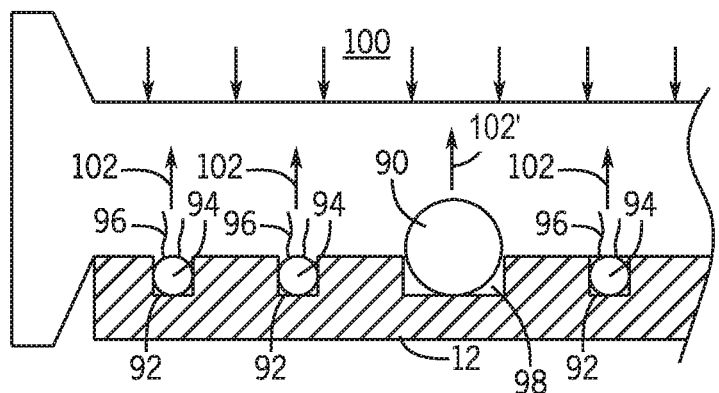
FIGS. 8A-8C are cut-away, partial sectional views of a portion of the array of FIG. 7 illustrating beads or other structures deposited in the array to form the fiducial feature.
Figure 8B:
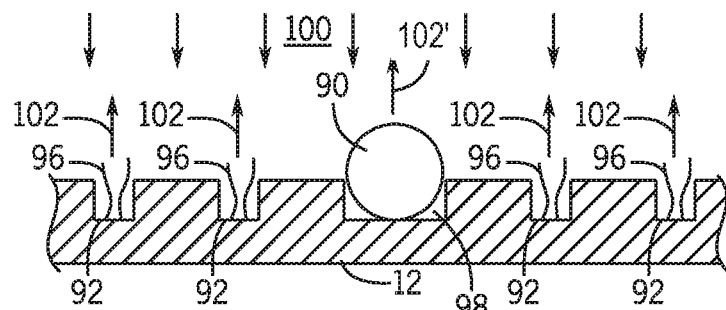
Figure 8C:
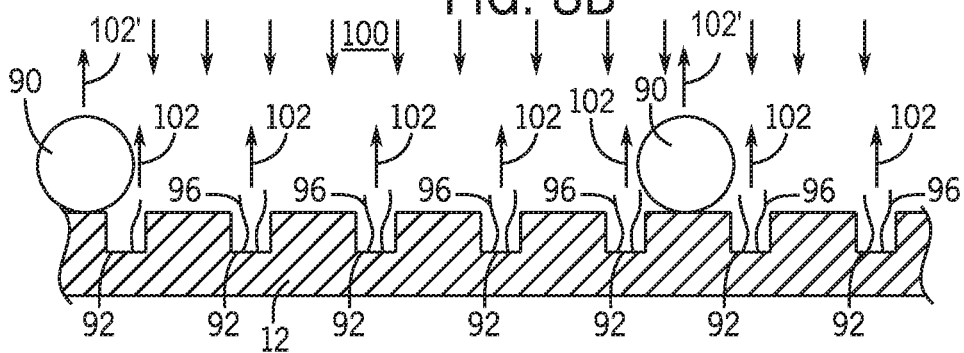

In an example, a fiducial of the "always on" type may be made up of beads that are specifically located in the support as illustrated in FIGS. 8A-8C. As shown in the FIG. 8A, wells or depressions 92 are formed in the support or substrate of the patterned array 12. Beads 94, or other molecular supports, may be disposed in these wells 92. During use, molecules of interest, as indicated by reference numeral 96 are anchored to the beads 94, such as for analysis, sequencing, characterization, and so forth. Additional wells 98 are formed in the substrate or support for larger structures, such as the beads 90 that will form the fiducial. It may be noted that for configuring such patterned arrays 12, it may be desirable to form both the larger and smaller wells 98, 92 and to process the support for attachment of the beads 90, 94, wherein the larger beads 90 are introduced into the wells 98 before the smaller beads 94 are disposed into their wells 92. The beads 90 will be too large to become lodged in the smaller wells 92, and are thus located in the desired fiducial configuration as defined by the larger wells 98. In practice, the wells 98 may be combined to form a trench in which the beads 90 are lodged. In either case, the wells or trench may be formed by any suitable process, such as ion etching or nanoimprint lithography. By way of example, about 0.5 µm to about 10 µm diameter microspheres may be self-assembled in a trench prior to introduction of analytes into the array. In some cases, it may be desirable to use one-dimensional arrays of wells rather than a trench to enhance complete filling of the fiducial shape by the spheres, and to avoid removal of the spheres by fluidic forces. Moreover, any suitable materials may be used for the beads or spheres, such as polystyrene or silica or combinations thereof, that can be assembled into a variety of patterns by filling trenches or wells, as described. Materials such as colloidal spheres may be useful for rigid substrates (e.g., silicon or glass). During auto-assembly, spheres that do not enter wells or trenches can be removed by a receding contact line (e.g., by flowing air past the surface) or by flow wash.

In other examples shown in FIGS. 8B and 8C, beads 90 may be located on the support, as in the example of FIG. 8A, but the material of interest 96, such as biological molecules, may be located in locations without the use of beads or similar supports. In the example of FIG. 8B, wells 92 are formed, here again, and the material 96 is disposed in these wells. In other examples, the material 96 may be disposed on a top surface of the support without such wells 92. In the example of FIG. 8C, the beads 90 may be located on the surface of the support, either in desired locations, or randomly. In use, such fiducials will again appear in the image data, and once located in the data can be used through successive cycles of imaging or detection as location aids (that is, though not initially in known locations, their location will be detected and thereafter used for reference).

Moreover, while spheres or beads have been referred to in the foregoing discussion, the elements forming the "always on" fiducials need not be spherical. Other shapes, such as cubes, blocks, and non-spherical shapes may be used. Moreover, the fiducial shape need not be ring-like, but may be any desired shape, such as a rectangle or cross. As for the size, here again, any desired size may be used, such as from about 5 µm to about 100 µm. Spacing between such elements may be uniform or non-uniform.

Such fiducials, in use, allow for signals to be returned at all phases of imaging. For example, the beads 90, or a coating provided on the beads may exhibit an absorption spectrum and an emission spectrum that permits them to be excited by the different wavelengths used for imaging of the site beads so that regardless of the excitation radiation wavelength, signals are returned from the larger beads 90. In the images of FIGS. 8A-8C, for example, the excitation radiation is illustrated by arrows 100, while the return signals 102, 102' emanate from the molecules of interest 96 and the fiducial (e.g., bead 90). As the different wavelengths of radiation 100 are used during sequential operations of imaging, then, some of the molecules 96 will return signals 102, depending upon the tags used during the imaging operation, while the fiducial beads 90 will return signals 102' at all imaging operations, enabling localization of the sites for indexing and molecular characterization regardless of the excitation wavelength.

In general, such "always on" fiducials may be made up of autofluorescent microspheres. In such cases, the fiducials will be observable in the absence of signals from the array or patterned for which the fiducials are registered.

Figure 9:
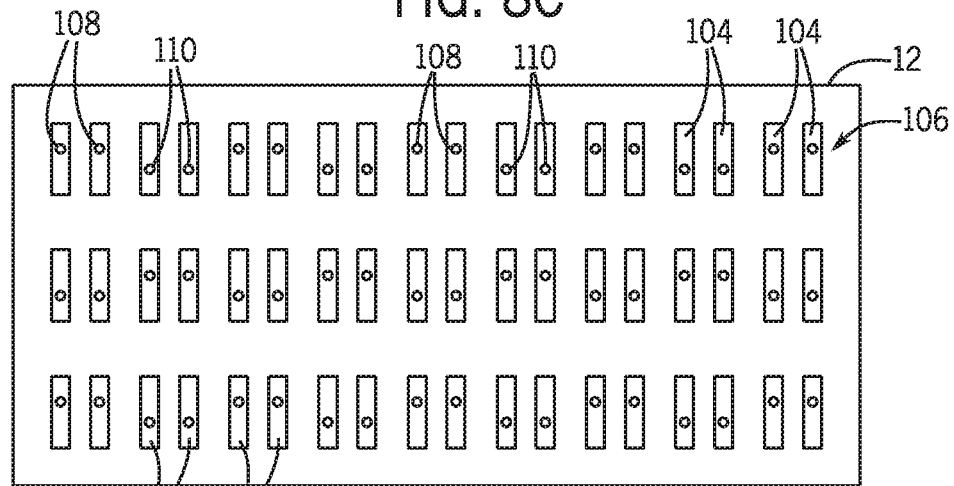
FIG. 9 is a simplified overview of a patterned array illustrating a number of site regions and fiducials formed in the site regions in a defined pattern.

Such fiducials, and indeed any of the fiducials disclosed in the present discussion, may be laid out in any one of many desired patterns and relationships that may, themselves, provide useful the information and facilitate processing of data. FIG. 9, for example, illustrates fiducials disposed in alternating positions within swaths of sites on a patterned array support. In this example, sites 104, or as illustrated swaths 104 of sites, are provided on the support of the patterned array 12. The fiducials are provided at alternating positions in each row 106 of sites or swaths 104. As illustrated in this example, fiducials 108 are provided in pairs of swaths 104, alternating with fiducials 110 provided at other positions within adjacent pairs of swaths 104. Such arrangements may facilitate localization of the fiducials, such as where the fiducials are configured, as in the case of the "always on" fiducials discussed above. While two alternating positions are shown in FIG. 9, it should be realized that other numbers of positions may be utilized, including fiducials that can be localized and distinguished from other locations on the support by virtue of their locations within the swaths, their locations with respect to other fiducials, and so forth.

Figure 10:
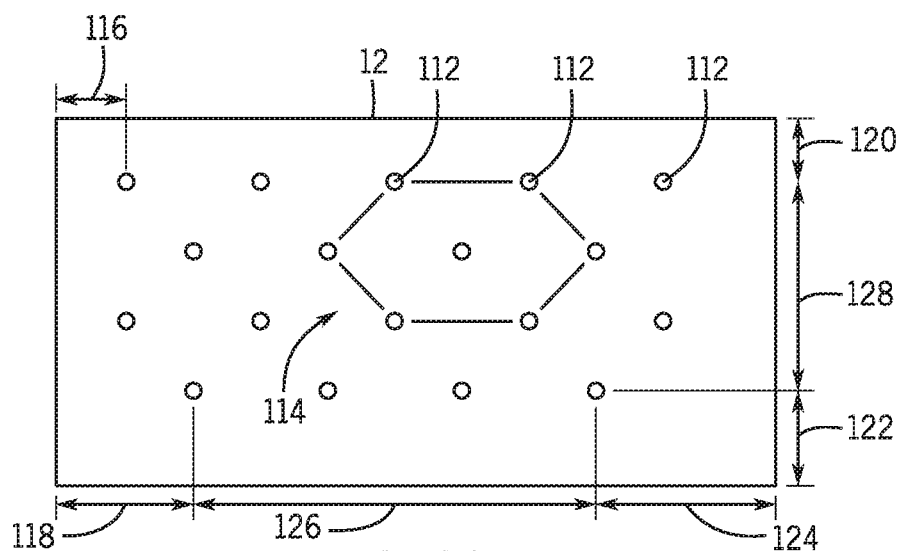
FIG. 10 is a diagrammatical view of an example patterned array having fiducials laid out in a regular pattern.

Another example useful layout for fiducials according to present techniques is illustrated in FIG. 10. In this example, the fiducials are disposed in a regular, repeating pattern. In general, such patterns may be considered as tessellated patterns which may or may not repeat, or that may repeat in desired dimensions, positions, orientations, and so forth, or in a repeating fashion, but with some repetitions having different dimensions, positions, orientations, and so forth. In the example illustrated in FIG. 10, the patterned array 12 has a series of fiducials 112 formed in the surface where the sites or swaths may be provided (not shown in the image for clarity). In the example shown in FIG. 10, the fiducials 112 are laid out in a hexagonal pattern that may form a regular hexagon, or as illustrated a flattened hexagon 114. Any other useful repeating patterns may also be employed. In the illustrated example, the fiducials 112 to the left begin a desired distance 116 from the left edge, while the next fiducials 112 begin at a different distance 118 from the same edge. Similarly, a first occurrence of the fiducials 112 from the top edge is at a distance 120 from the edge, while the bottom-most fiducial 112 is positioned at a distance 122 from the bottom edge. The fiducial 112 may be positioned from the right-most edge by a distance 124. In general, inter-fiducial distances may be selected as indicated by reference numerals 126 and 128 to provide the desired pattern, as well as the position and orientation of the pattern with respect to known edge locations. The pattern may also be located specifically with reference to a different type of fiducial, such as the corner fiducial discussed above for coarse positioning. This layout, and variations on the layout, such as with respect to known locations such as the edges, may facilitate in determining the locations of the fiducials, and prevent or reduce the likelihood of errors in localizing the fiducials and image data. It should be noted that the term "hexagon" may be more generally understood as other than a regular shape, including layouts that are simply "staggered" or otherwise displaced from a regular rectilinear pattern.

It should be noted that the number of fiducials used in an array may be selected to enhance reliability and robustness in imaging and analyzing the sites of an array. For example, the layouts discussed here could be used with as few as three fiducials, although a larger number allows for robustness due to the likelihood that at least three fiducials will be reliably detected in case at least one of the fiducials experiences some anomaly in imaging or recognition (e.g., due to bubbles, out-of-focus regions, etc.). The fiducial count and sequencing accuracy could be increased, for example, by using the non-rectilinear arrangements (e.g., hexagonal) discussed here. It may be useful as well to lay out the fiducials to be equidistant from a center point because the non-linear distortion is radial and this arrangement imparts the same distortion on all fiducials. Regarding the number of fiducials used, if a minimum of 3 is desired, for example, use of 4 may allow for avoiding anomalies with 1, while the use of 6, for example, allows for avoiding anomalies with 3.

The layouts discussed here may also address a challenge with skew in patterned flow cells and fiducials. For example, software and routines used to determine the affine transform for correction of location data expect fiducials to be in known locations. Skew within the flow cell over the length of a scan can result in fiducials moving from the expected areas towards the edge of the field, which may cause inaccuracies due to large extrapolations and non-linear distortion. Robustness to large skew can be obtained by placing fiducials over the whole patterned area and switching the fiducials used based on the fiducials that are most centered in the field of view.

Moreover, the examples described for both the form of each fiducial (e.g., multiple adjacent or nested shapes) and their layout have the potential to increase sequencing accuracy by locating the fiducials more accurately, leading to lower positioning error on cluster or site locations, improved intensity extraction, and more accurate basecalling in sequencing applications.

Still further, in "point-and-shoot" imaging systems, the imaging area tends to be more square and the optical distortion tends to be radial. For such reasons, conventional fiducial layouts may be less than ideal because fiducials at different distances from the image center may have different amounts of optical distortion. A design that is more appropriate for point-and-shoot systems may be a hexagonal layout as described, e.g., in reference to FIG. 10.

As mentioned above, depending upon the skew of a flow cell and sequencing instrument, fiducials may not appear at expected locations. This presents challenges for the processing routines in finding the fiducials. As also mentioned, if they are found, the affine transformation may not be accurate if a significant extrapolation is done or the fiducial shape is perturbed by non-linear optical distortion. In such cases, a hexagonal layout may be used with a region in which a "center" fiducial lies in a central or inside position within the hexagon of fiducials. If the processing system is able to determine the skew of the flow cell (e.g., from auto-centering fiducials), it can switch between the specific fiducials used based on this hexagonal or modified hexagonal layout (e.g., additional fiducial in the center region).

Figure 11:
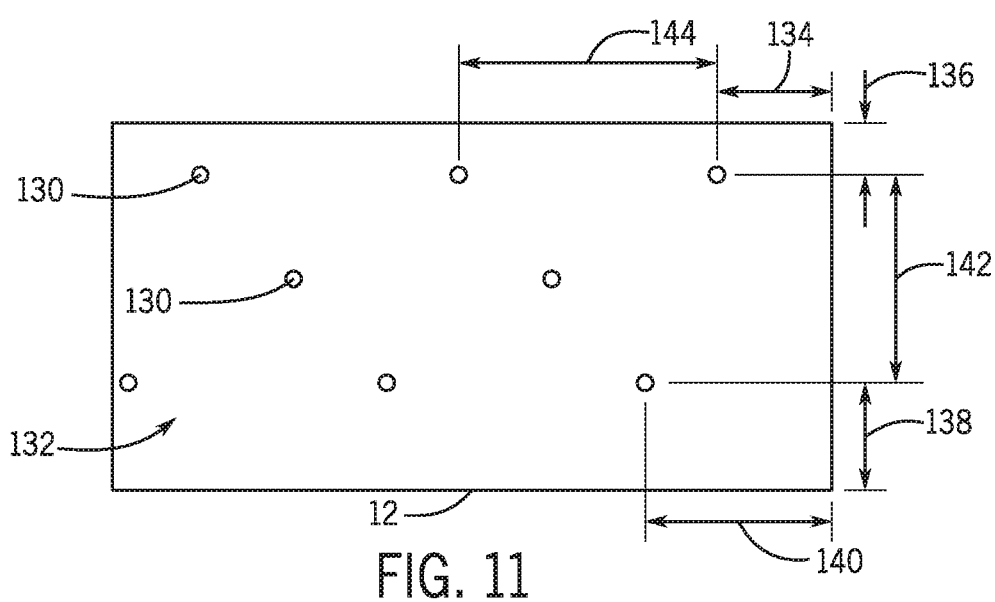
FIG. 11 is a further diagrammatic representation of an example patterned array having fiducials disposed in a non-regular layout.

Another possible layout for the fiducials is illustrated in FIG. 11. As shown in this example layout, a non-repeating arrangement of fiducials 130 may be provided (here again, the sites or swaths have not been shown in the figure for clarity). In this example, the array 12 has a number of fiducials 130 that are positioned on or in the support and that are located at different distances from one another to provide positions from one another and from known features, such as the support edges. By way of example, an upper-right fiducial is located distances 134 and 136 from edges that meet in the upper right corner. A lower-right fiducial is positioned at distances 138 and 140 from edges that meet in a lower right corner. These fiducials are spaced from one another by a distance 142. Other inter-fiducial distances 144 may be used between the different fiducials 130. Each fiducial 130, then, may be located a distance from a known feature, including the other fiducials 130. In this example, the region 132 represents a periodic underlying array to which the locations of each of the features may be registered, through the use of the large fiducials 130. The distances and directions of the fiducials 130 with respect to these known features and with respect to one another may be cataloged and used for localization of the fiducials in image data, localization of the fiducials with respect to sites, indexing of sites with respect to the fiducials, and so forth. The layout may also allow for locating one or more of the fiducials with respect to other fiducials that are located in the image data. It should also be noted that in some implementations, fiducials may be located in regular patterns, with some fiducials being located in non-repeating locations with respect to the patterns. That is, not all fiducials may be located in the regular pattern, or not all fiducials may be located in a non-repeating layout.

FIGS. 12A-12G illustrate example layouts for fiducials that may allow for improved detection and location. In some systems, accuracy and mitigation of some error modes of the sequencing instrument may be achieved by using such layouts. In line scanning systems, for example, changes may be made from a rectangular layout to one with fiducials staggered over the image area. In systems employing a stage for supporting a flow cell, for example, if the stage does not scan properly when imaging, fiducials in a regular rectangular layout may be lost. As illustrated in FIG. 12A, for example, for an image area of an array 12, two fiducials 112 in a rectangular pattern P may be negatively impacted by problems with the stage, rendering difficult, inaccurate, or impossible the development of an affine transform for site location correction. In examples utilizing a staggered layout P', however, as illustrated in FIG. 12B, a single fiducial 112 may be inaccurately or improperly located, but it is more likely that the other three fiducials 112 in the image area will remain accurately detected and located for use in the affine transform computation.

In another example, shown in FIG. 12C, the fiducial count in an image area may be increased to provide enhanced robustness in the event that fiducials 112 are unusable (such as due to bubbles present, or out of focus regions of the image and resulting data). This may be useful, for example, with line scanning systems. In the example of FIG. 12C, a layout P" includes 6 fiducials 112 in a rectangular layout in the image area. In this case, as many as 3 fiducials may be unusable for any reason while maintaining the ability to compute the affine transform. Similarly, combining the approaches of FIGS. 12B and 12C, FIG. 12D illustrates a further layout P'', in which the 6 fiducials 112 are present in the image area, but staggered to provide further improvement.

On step-and-shoot systems (sometimes called "point-and-shoot"), imaging areas tend to be more square (a rectangle with sides that are equal or not very elongated), and optical distortion tends to be radial. For such systems, it may be useful to employ layouts that provide fiducials 112 at a uniform distance from an image center, as illustrated in FIG. 12E. In this example, more than 4 (e.g., 6) fiducials 112 are used in an image area of the array 12, such as in a regular hexagonal pattern 114'. This arrangement provides both the robustness of an increased number of fiducials in the image area (in the event that up to 3 fiducials are unusable for any reason) as well as uniform distance from a center of the area.

Further, depending upon skew of the flow cell and the sequencing instrument, fiducials may not appear in expected locations. This presents challenges for the analysis process (e.g., in locating the fiducials). If they are found, the affine transform based on the fiducial locations may not be accurate if significant extrapolation is done, or if the fiducial shape is perturbed by non-linear optical distortion. FIGS. 12F and 12G illustrate an example of a fiducial layout 114'' that may improve location and processing in such situations. The layout 114'' here is based on a hexagonal pattern with a fiducial 112 at the center of the hexagon (although partial hexagons may be provided—or the layout may be thought of as rectangular with respect to every other row, with an interposed row in which fiducials 112 are located at midpoints between neighboring fiducials 112 in the rectangular rows). In a case where the flow cell is well-centered in the instrument, the layout 114'' may be used as illustrated in FIG. 12F, that is, by selecting 5 fiducials 112 in an image area S with one of the fiducials 112 generally in the center of the area. In the case of skew (particularly large skew) of the flow cell in the instrument, which may be determined, for example, by auto-centering fiducials near inlet and outlet sides of the flow cell, the system may base calculations on a reduced set of the fiducials, such as 4 fiducials 112 in the image area S', as illustrated in FIG. 12G. In either case, the ability to switch between which fiducials 112 to use in different cases of skew is enabled by the layout 114'' of FIGS. 12F and 12G.

It may be noted that a similarity of the layouts of FIGS. 12B, 12D, 12E, 12F and 12G is that the fiducial features 112 are disposed in rows that are offset with respect to one another. In these offset rows, the fiducials 112 of a first row do not align with fiducials in an adjacent row along a line perpendicular to the first and second rows. The resulting pattern may be triangular, hexagonal, or even irregular.

Regarding the layouts discussed above, it may be noted that in some sequencing systems, the fabrication of the support and array (e.g., the flow cell), imaging of the sites, and processing of image data may be based on a periodicity that is matched to tiling and stitching that is performed in the image data (e.g., for adjacent image areas). Significant effort may be invested in ensuring alignment of certain features, such as lanes of the sites with an interposer layer of the support. By using one of the layouts discussed above, tighter patterns may be considered, with sufficient fiducial density allowing for always having sufficient fiducials for proper location and correction of location errors free from the periodicity concerns, or at least being much more robust than current layouts even if some fiducials are for any reason not reliable. Moreover, in existing technologies, for imaged tiles, if it is unknown where to expect fiducials, it can be very time consuming to locate them by image analysis alone. In layouts where the fiducials are in approximately the same locations from tile to tile (assuming the flow cell is well designed, assembled and aligned), this is less of a problem. However, for certain approaches to layout, such as those described here, which may include different periodicities, or where fiducials are continuously distributed to allow for reduced tolerances on alignment between surfaces of the flow cell, positions may be precomputed for all fiducials on the flow cell relative to a global registration done before sequencing begins (for example, by locating auto-centering fiducial crosses). Then, although the imaged tile may yield different locations of fiducials from tile to tile (e.g., due to poorly aligned layers of the flow cell), the expected locations of the fiducials can be known a priori, and the image processing of each tile may be based on a list of expected coordinates for the fiducials of each tile. This functions as a coarse alignment process in which the actual fiducial registration algorithm provides finer alignment of each tile. For cases where the fiducials are truly in a random distribution, a priori knowledge of their location may not be possible, and registration is similar to that for randomly patterned flow cells (e.g., execute several cycles of sequencing and imaging, cross correlate the images to extract locations of the fiducials in each tile, and for the subsequent cycles, provide the determined coordinates to each tile).

In addition to the foregoing signal response characteristics and layouts, fiducials may be formed in ways that allow for distinct advantages over conventional configurations. Moreover, it should be noted, through the present discussion, that these aspects of the techniques are not mutually exclusive. That is, the forms and configurations discussed below may be used with one another, with "always on" technologies, in desired useful layouts, and so forth.

Figure 13:
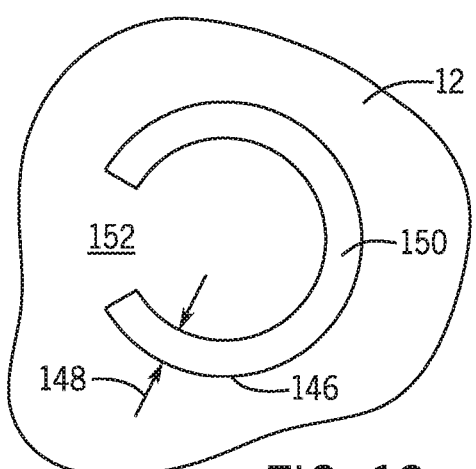
FIG. 13 is a detailed view of an example fiducial having a non-closed shape or configuration.

A first configuration for a potentially useful fiducial is illustrated in FIG. 13. In this example, the array 12 has an open or non-closed shaped fiducial 146. The fiducial 146 may have desired characteristics or features, such as a thickness or width 148, a partially non-closed segment 150, and at least one opening 152. The shape used for the fiducial 146 may be circular, as shown in this example, or may be any other desired shape (e.g., elliptical, box-shaped, etc.). In general, the "non-closed" configuration means that the shape has at least a portion that extends over 180° to at least begin to enclose a region that may be considered an "inner" region. Many such shapes may be envisaged, as distinguished from open shapes that do not begin to enclose an inner region, or fully closed shapes that do not include the opening 152.

Figure 14:
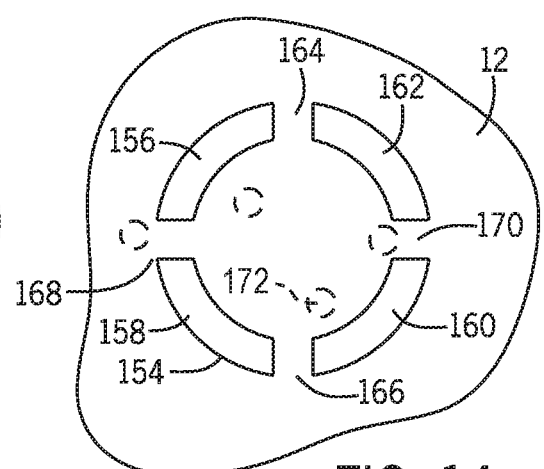
FIG. 14 is a further detailed view of an example fiducial having a non-closed shape to improve manufacture and processing of a patterned array.

Another example configuration for a potential useful fiducial is illustrated in FIG. 14. In this case, the fiducial 154 has segments that form a partial barrier and that partially enclose an inner region. In this sense, the fiducial 154 of FIG. 14 may be thought of as a special case of the non-closed shape discussed above. It is noted, however, that it is the combination of the segments that partially enclose the inner region. In the case of FIG. 14, four such segments are provided, including segments 156, 158, 160, and 162. These segments 156, 158, 160, and 162 are separated from one another by openings 164, 166, 168, and 170. In this case, the segments 156, 158, 160, and 162, though separated, form a circular fiducial, although any desired shape may be used. In addition to the benefits of the non-closed shape, the openings 164, 166, 168, and 170 in the fiducial 154 of FIG. 14 may permit improvements in the manufacture of the patterned array. In some manufacturing techniques, such as imprint lithography, bubbles may form in the material imprinted, such as in or near the fiducials. The use of the non-closed arrangements for the fiducials may allow for the escape of such bubbles (indicated by the dashed circles 172 in the figure) or the avoidance of the formation of such bubbles altogether.

Figure 15:
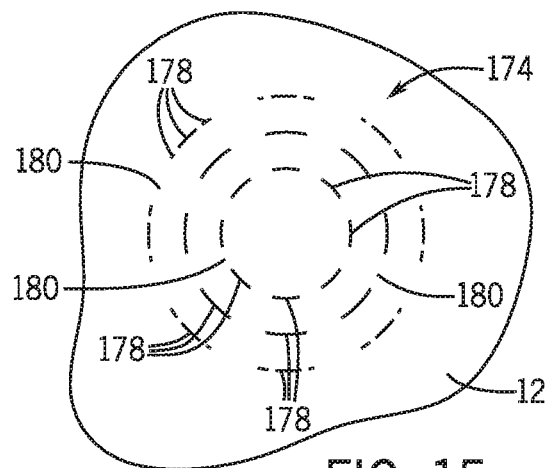
FIG. 15 is a further detailed view of an example fiducial having a series of non-closed shapes.

FIG. 15 illustrates a further example of a fiducial 174 that comprises a series of non-closed shapes. The shapes are circular, as before, although any desired shape may be used. Each of the shapes comprises segments 178 separated by openings 180. In the example of FIG. 15, the shapes are concentric circles, although the shapes need not be strictly concentric, but may be offset from one another as discussed below. Moreover, the openings 180 provided in each of the shapes may be sufficient to allow the passage of bubbles and fluid-borne constituents as discussed above. It should be appreciated that the thickness or width of the segments 178, the spacing between segments 178 of each shape, and the spacing between adjacent shapes may be selected to permit the fiducial 174 to be more easily identified, localized, or to convey information by virtue of the configuration as discussed more fully below.

Figure 16:
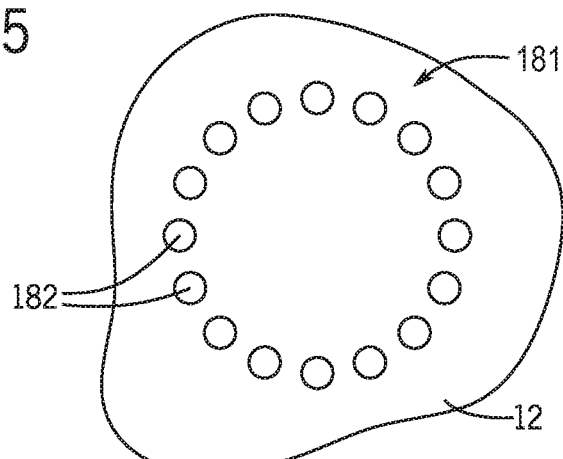
FIG. 16 is a detailed view of an example fiducial having a non-closed shape formed of dot-like structures.

FIG. 16 illustrates a further example for a fiducial 181 that comprises a series of dots 182. Here again, this may be considered a special case of a non-closed shape and may facilitate manufacturing, utilize less surface area of the array 12, or provide other benefits, while permitting the passage of bubbles or fluid-borne constituents.

Figure 17:
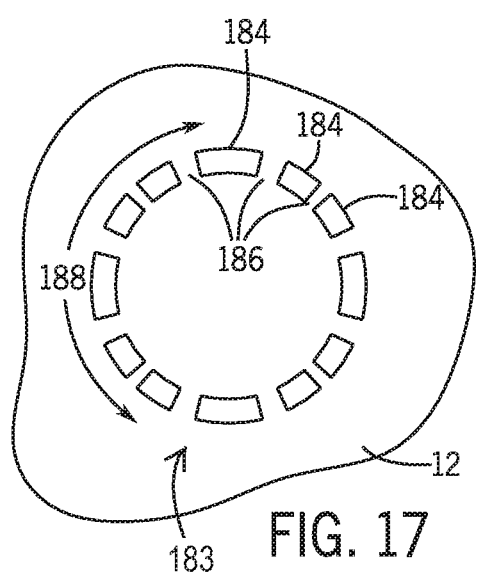
FIG. 17 is a further detailed view of an example fiducial having a non-closed shape and forming segments that may convey data, such as barcode-like encoding.

As noted, it is contemplated that some examples of the fiducials may encode or provide information that can be useful in many different ways. The encoding of such data is provided by selection of parameters or characteristics of the fiducial that are apparent in image data (e.g., by the distinction between light and dark regions in the image data). Here again, such fiducials may be of the "always-on" type so that this information is conveyed in all images produced. Some parameters that may be used for data encoding have been discussed for the fiducials described above (e.g., width or thickness, size and shape, distance between a number of shapes, etc.). Others may be apparent from the fiducials of the following figures. FIG. 17 illustrates a fiducial 183 that is non-closed in shape, comprising segments 184 separated by openings 186. Here again, the thickness or width of each segment 184 may be adjusted to enhance detection or to provide information. More than one such shape may be used, and these may be concentric or non-concentric. In the example of FIG. 17, the segments 184 are disposed adjacent to one another and are different in length or extent around at least a portion of the fiducial as indicated by reference numeral 188. The extent of the segments 184, and spacings between the segments may be selected to provide information in accordance with a standard and well-understood encoding technique. The information provided by the fiducial 183 may include any useful data, such as identification of the fiducial, identification of a location of the fiducial, indications of where to locate other fiducials, identification of the array, identification of a person or subject providing biological samples for the array, manufacturers, manufacturing batches, or any other useful information.

Figure 18:
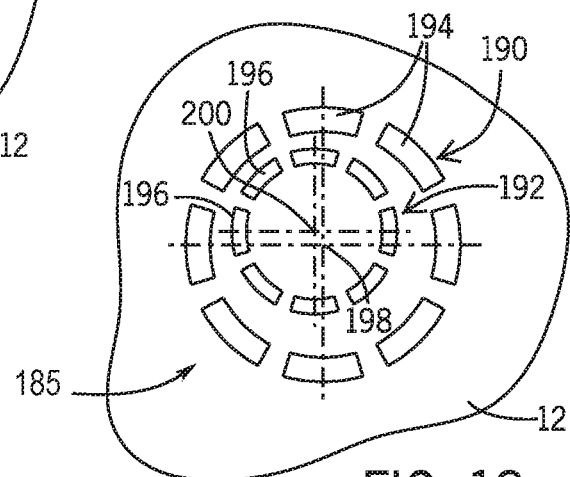
FIG. 18 is a detailed view of an example fiducial having two non-closed shapes that are non-concentric.

FIG. 18 illustrates a further example for a fiducial 185, which here comprises two shapes that are not concentric with one another. It should be borne in mind that this configuration, or variations of this configuration may be used with any of the other techniques disclosed, such as for "always-on" fiducials, non-closed or closed shapes, segments providing data, segments and openings allowing for the flow of fluids, and so forth. Moreover, any desired shapes may be used, with the circular shapes shown being only one possibility. In the example of FIG. 18, the shapes are non-concentric. The outer shape 190 is a ring that at least partially surrounds an inner shape or ring 192. The outer shape 190 comprises segments 194 separated from one another by openings, while the inner shape 192 also comprises segments 196 separated by openings. The outer shape 190 has a center 198 that is offset from the center 200 of the inner shape 192. It is presently contemplated that, again, the non-closed shapes may allow for the passage of fluids, while presenting the potential for encoding information by virtue of the physical parameters that characterize the shapes, their relationship to one another, and in this case, the offset between their centers 198, 200. For example, the offset may facilitate identification of the fiducial 185, determination of its location on the array 12, determination of the location of other fiducials or features, and so forth.

FIGS. 19A-19D illustrate a further example for a fiducial 226 that may facilitate this type of information conveyance, such as localization of features. In this example, a fiducial 226 comprises a larger feature 228 and a smaller feature 230. In this case, the smaller feature 230 is located within the larger feature 228, and in this example both are ring-like structures. The features or shapes are both adjacent and nested in this example. As before, such structures may be closed shapes, non-closed shapes, "always-on" structures, or may utilize any of the other configurations disclosed herein. In the example of FIG. 19A, an interior space 232 is at least partially surrounded by the larger feature 228, and has a center 234. A center 236 of the smaller feature 230 is offset from the center 234 by a distance 238. Moreover, a projection through the two centers 234, 236 defines an angle 240 with respect to a known orientation, which, in the illustrated example, is the vertical dashed line. Such fiducials 226 may be useful for conveying information, such as their location in an array 12, their location with respect to edges (of the array or one or more swaths), the location of other features (including other fiducials), the direction of such features (e.g., by virtue of the angle of the projection), the distance to features (including fiducials) by virtue of the distance of the offset, and so forth.

The example of FIG. 19B is a similar adjacent and nested arrangement as shown in FIG. 19A, but in this case the larger feature 228 and the smaller feature 230 overlap. This overlap may facilitate localization of the fiducial 226', determination of the orientation or direction of the offset, and so forth. The overlapping region 242 in this case is aligned with the angle of offset, the amount of offset 244 being defined by the relative sizes of the features 228, 230.

In the example of the fiducial 226" shown in FIG. 19C, a similar adjacent and nested arrangement includes a larger feature 228 and a smaller feature 230. In this case, the interior space 232 of the larger feature 228 includes only a portion of the smaller feature 230, which extends outside the larger feature 228 to form overlapping regions 246. An offset 248 is here again provided, which may assist in identifying the features 228, 230, identifying the location, or providing information regarding locations and distances to other features in the array 12. It should be noted that arrangements of the type shown in FIG. 19C may comprise differently sized features, or the features may be of the same size, but with offset centers 234, 236 and at desired angular orientations.

In the example of FIG. 19D, the fiducial 226''' comprises a first, larger feature 228 and a smaller feature 230, in this case both circles (although other shapes again could be used). The two features 228, 230 are adjacent to and offset from one another, but in this example do not overlap. As in the previous examples, each feature 228, 230 may have a center 234 and 236 that may be used as a reference for a direction. That is, as in the preceding examples, a projection through the two centers 234, 236 defines an angle 240 with respect to a known orientation, which, in the illustrated example, is the vertical dashed line. Such fiducials 226' may be useful for conveying information such as their location in an array 12, their location with respect to edges (of the array or one or more swaths), the location of other features (including fiducials), the direction of such features, the distance to features (including fiducials), and so forth. It may be noted that, other than in the "nested" arrangements, although reference is made to "larger" and "smaller" features, where the features are not "nested", they may be the same size.

The foregoing fiducial arrangements may have a number of advantages. For example, the offset or displaced rings or features may define a vector, the direction of which connects the centers of the rings or features and encodes a desired orientation of the substrate (or any other useful direction). Encoding the orientation of the substrate in this way may simplify manufacture of flow cells because image registration can be made to be skew-tolerant even when only imaging 1-2 fiducials. Therefore, manufacturing tolerances on alignment of the different layers of the flow cell during assembly, and on alignment of the flow cell to the sequencer, could be greatly relaxed. In these examples, both rings remain rotation invariant (i.e., the kernel will overlap with the image regardless of the orientation of the substrate). Then the "center" of the fiducial may be referred to the center of the outer ring. The direction is calculated by finding the vector angle between the centers of the outer and inner rings, as mentioned.

Figure 20A:
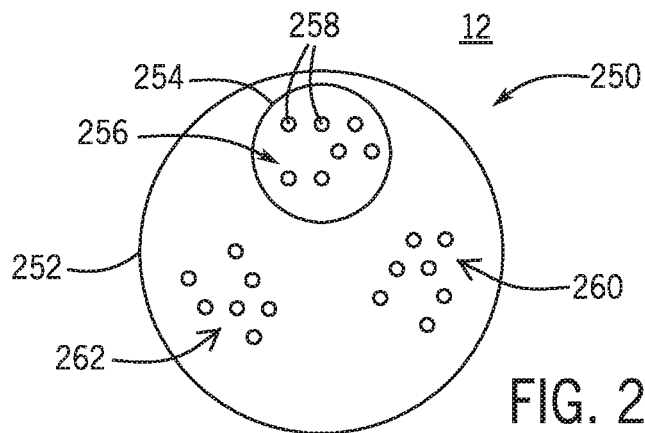
FIG. 20A is a detailed view of an example fiducial having data encoding features.
Figure 20B:
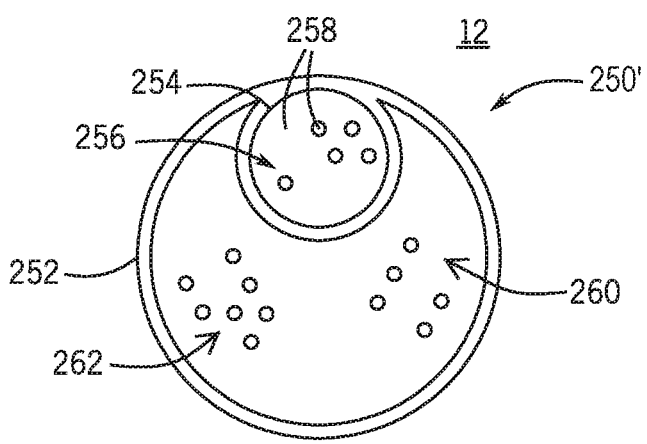
FIG. 20B is a view of the fiducial imaged in a manner that provides robust decoding of the features.
Figure 20C:
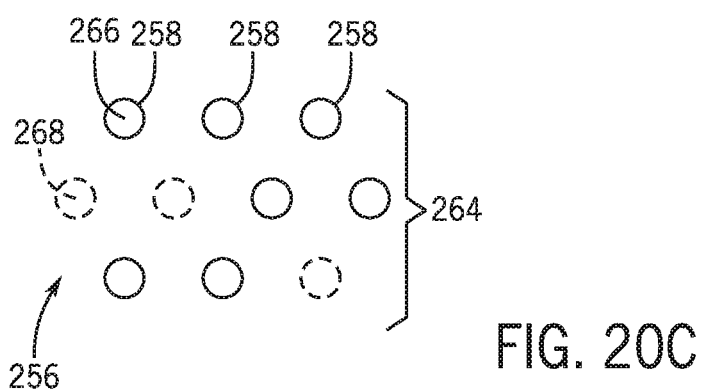
FIG. 20C is a diagrammatic representation of example features for encoding the data in the examples of FIGS. 20A and 20B.

Further, examples of fiducials that directly encode information may have a variety of forms and configurations, such as those shown for the example of FIGS. 20A-20C. The illustrated fiducials 250, 250' may comprise a larger feature 252 and a smaller feature 254. Within each of these features 252, 254, in the example illustrated, information may be encoded in novel ways. For example, three redundant sets of dots are provided in the illustrated approach, including a first set 256 made up of an array of dots 258 in the smaller feature 254, with similar redundant sets of dots 260 and 262 in the larger feature 252 outside the smaller feature 254. In practice, as few as one (a single) coded array may be employed, and the technique for encoding may take any desired form, including dots, areas, relative regions of light and dark in the images, and so forth. In all cases, such encoding may be machine readable.

Such direct encoding may employ digital, binary technologies wherein regions encode data based upon whether they return a signal (e.g., appear bright in image data) or do not return signal (e.g., appear dark in image data). A dark region where a signal could be expected may represent a "0", while a region that does produce a signal may represent a "1". Values or encoding may, of course, be determined based upon location within the array, orientation, size, and so forth. Those skilled in the art will readily recognize that such arrays may be defined to encode numbers, alphanumeric values, hexadecimal values, and so forth. The underlying data encoded may be representative of any desired information, such as identification of the fiducial, identification of the array, identification of a swath or location in the array, identification of locations or directions of other features, identification of subjects or individuals (e.g., who provided samples for testing), identification of a manufacturer or manufacturing details, dates, institutions, and so forth.

It is presently contemplated that the use of redundant features of this type may enhance the robustness of the identification. For example, as shown in FIG. 20B, the three sets of dots 256, 260, 262 of FIG. 20B may, during imaging, fail to correspond exactly to one another. That is, despite being identically formed or intended, for various reasons some of the dots may appear when not desired, or may not appear where desired. Algorithms for reading, interpreting, and comparing the decoded data may provide identification and data output in such cases based upon the redundancy.

FIG. 20C illustrates an example of an array of dots 258 for directly encoding information in a fiducial of this type. The array (or set) 256 comprises dots 258 arranged in a known pattern 264. The dots 258 may be populated with beads or other materials that respond or do not respond to wavelengths of radiation utilized in imaging. In some cases, it may be desirable to utilize materials that have absorption and emission spectra that overlap with the different wavelengths of radiation used in imaging so that the array/set 256 is "always on". In the example illustrated, dots 266 are populated to return signals, whereas dots 268, at other locations, that could be populated are not populated or are populated with a material that selectively does not return a signal. The resulting array, then, will return collective signals that encode the desired data directly. Here again, encoded data may be machine readable.

In practice, such examples may present encoding by desired schemes. For example, each "1" is represented by a large microwell that produces a signal, or appears "white" in image data. Each "0" is represented by an absence of a microwell. In the example illustrated in FIG. 20C, the number four hundred eighty seven (487) may be expressed as a 10-bit binary number, and then encoded into the 10 possible microwells (dots 264). The white microwells (e.g., dots 258) may be physically patterned (and clustered), while the black wells (e.g., dots 268, illustrated in dashed outlines) may not be physically patterned (they may remain flush with the interstitial area). In this way, only the 1's may be clustered and therefore seen on a sequencer. In the illustrated example, the layout of the binary number is from left to right, top to bottom. Binary encoding may be useful. For example, there is no ambiguity for each value. It is either completely dark, or has some region of fluorescence. A hexagonal layout is used to pack the bits closely together in the illustrated example so they take up less space, because they do not contribute to sequenceable surface area, so their overall area should be minimized. Moreover, binary encoding does not necessarily call for sophisticated image recognition. Once the fiducial is located, and its orientation ascertained, each well of the binary code can be located by overlaying a pre-calculated table of location values for each of the 10 possible microwells in the code (in this example). This simple location with no image recognition is made possible by the directional information described previously.

Ultimately, any type of arrangement, shape, or number of bits is possible. In the illustrated example, the bits were chosen to be substantially larger than individual wells so that they are not mistaken for sites, and have sufficient polyclonality that some portion of each bit will light up in each color channel (e.g., "always on"). It may be noted, here, that the use of polyclonality may have one or more drawbacks. For example, each of the microwells will be only partially populated (~25% occupancy) and therefore, errors can be introduced into the decoded value because one or more of the microwells may have too little occupancy in any one channel to properly register as a "1". Or, an area that should be a zero may be contaminated (or have surface roughness which can trap fluorophores) and still return a signal during imaging, despite having no microwell. These are commonly known as bit-flip errors.

A number of solutions may be provided for such challenges. For example, the intensities of all color channels may be summed to create a composite image. In this case, the probability of bit-flips due to polyclonality may be greatly reduced (but not entirely eliminated: there is still a chance that, due to clustering errors, or fabrication imperfections, a microwell may not cluster enough to appear bright enough in any color channel).

In another solution, error correction may be introduced, such as by redundancy. In the illustrated example, for example, the physical binary code is repeated three times, identically, in the fiducial (they can be placed anywhere, with any known orientation relative to each other and the fiducial). In the example illustrated, to simulate errors, wells were randomly obscured with a probability of 10% (the real value of this error rate will dictate how many times it may be desirable to repeat the code to capture errors). This may be expected to be a common type of error. In this example, wells were also randomly populated in the background (with 25% of the wells randomly selected to be bright—this simulates a single color channel in a 4-channel sequencing system). Then, two kernels were used for each of the rings to find the two centers and the orientation of the fiducial. This simulates how, after imaging, one may find the center and orientation of the fiducial. Next, knowing the positions of all physical bits relative to the fiducial, the image data pixels may be sampled to ascertain the value of the bit. In general, one may sample a predetermined number of pixels clustered around the centers of each physical bit (the area covered by the sampled pixels should match the area of the bit to gain as much signal as possible from each bit). If the aggregate intensity of the pixels for each physical bit passed a predetermined threshold value, it may be registered as a "1", otherwise, a "0". Once all three physical bits have been identified as 1's or 0's, each of the three codes was assembled into its corresponding binary number.

In the illustrated example, the errors resulted in three different values decoded for each code: 391, 487, and 230. Finally, a binary OR operation performed between all three numbers may enable the recovery of the originally encoded number. This triple-redundant error correction scheme can correct for up to two bit-flip errors, where the bit that should be a 1 is registered as a 0 (that is, a well that should be bright, was not bright enough and mistaken for dark). To correct more than two, quadruple or higher redundancy may be added.

Data encoding by features of the fiducials may be used, for example, to stitch multiple images together or to label different areas of a flow cell that are patterned with different conditions (e.g., different chemistries, different layouts of wells, etc.). To encode positional information, for example, a physically patterned, 10-bit binary code may be used for each fiducial as discussed above. On the flow cell, each microwell may by clustered and fluoresce in all channels of the sequencer. This binary code can be repeated multiple times in or near the fiducial (in the illustrated case, 3 times) to facilitate error-correction.

Figure 21A:
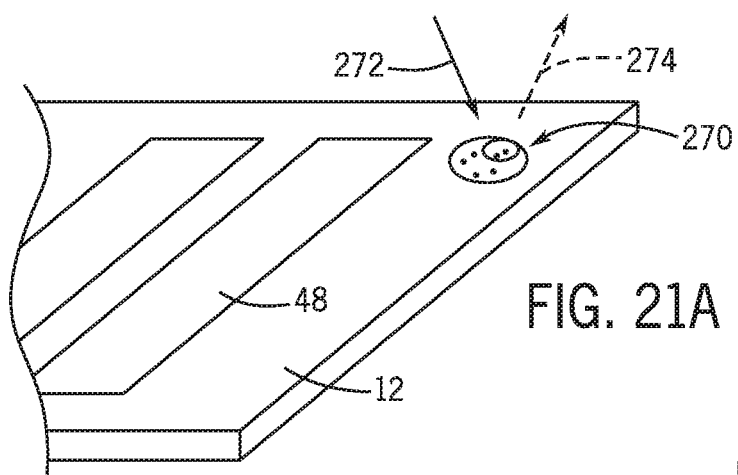
FIG. 21A is a cut-away, perspective view of a portion of an example patterned array having a fiducial that at least partially reflects radiation received during imaging or other processing.
Figure 21B:
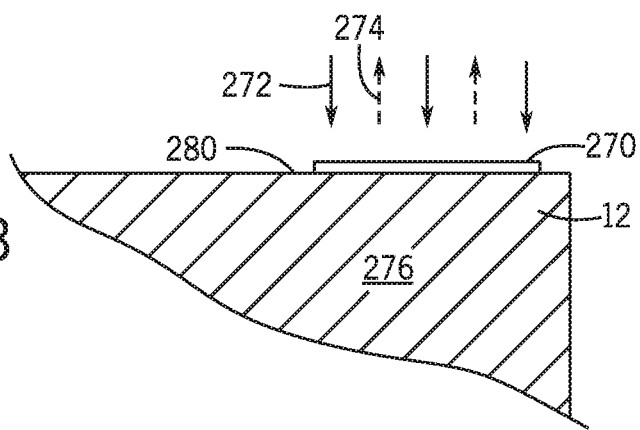
FIG. 21B is a cut-away, partially cross-sectional view of an example fiducial of the type shown in FIG. 21A.

Still further techniques for creating fiducials both for course alignment and registration of sites and other features may rely upon reflected radiation rather than emission resulting from excitation. Some of these fiducials may also encode information. FIGS. 21A and 21B illustrate a first example of such fiducials. In the example of FIG. 21A, a fiducial 270 is provided on a surface of an array 12. The fiducial 270 may be deposited on the support, such as by printing, engraving, vapor deposition, or by any other suitable technique. In such cases, the fiducial 270 may be made of a material, such as a metal, semiconductor, or other at least partially reflective material that reflects light at wavelengths utilized during processing, such as during imaging. The incident light 272 may originate from the optics of the imaging system 18 (FIG. 1), and reflected light 274 may be detected and utilized, such as, for aligning the array 12 in the imaging system 28, for providing encoded data as discussed above, or for any other useful purpose. Moreover, in this example and as shown in FIG. 21B, the fiducial 270 is affixed or disposed on the surface 280 of the array 12 rather than within the body 276 of the support.

Figure 22A:
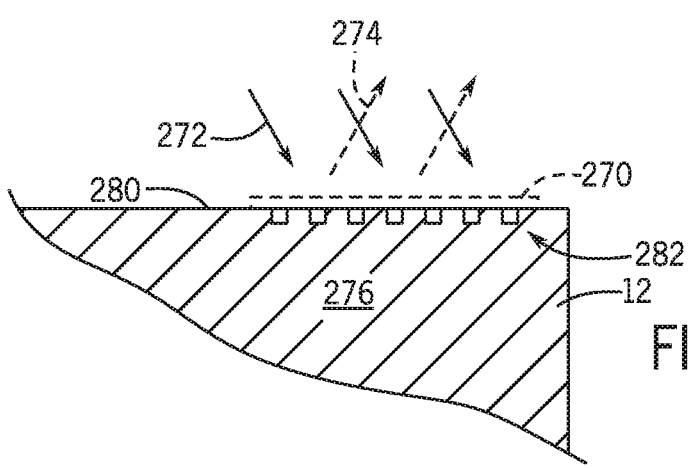
FIG. 22A is a cut-away, partially cross-sectional view of an example of a reflective fiducial that may include features that encode data or assist in imaging or processing, such as a Bragg grating.
Figure 22B:
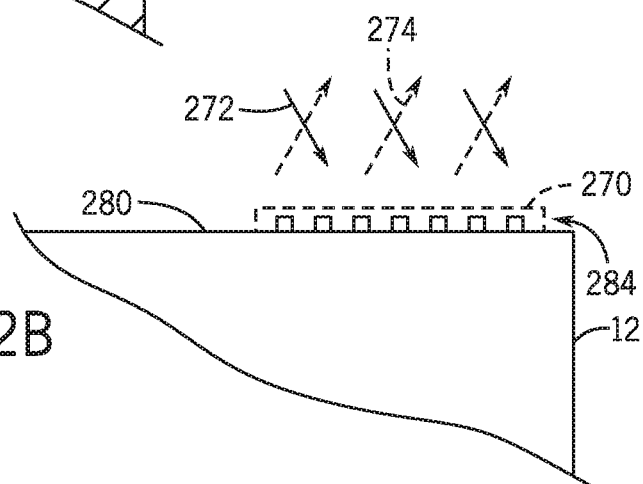
FIG. 22B is a cut-away view of an example of a reflective fiducial that may include features that encode data or assist in imaging or processing, such as a Bragg grating.

In other examples, such as illustrated in FIGS. 22A and 22B, fiducials 270 comprising reflective or refractive features may be formed on the surface 280, or within or partially within the body 276 of the array support. In the examples shown in FIGS. 22A and 22B, for example, the fiducials 270 comprise either troughs or ridges 282 or 284 that may themselves define data or information that can be interpreted, such as Bragg gratings. Such gratings may respond to specific wavelengths (or equivalently to frequencies) of incident light 272, and return reflected or refracted light 274 that is detected by the optics of the system and interpreted.

Figure 23:
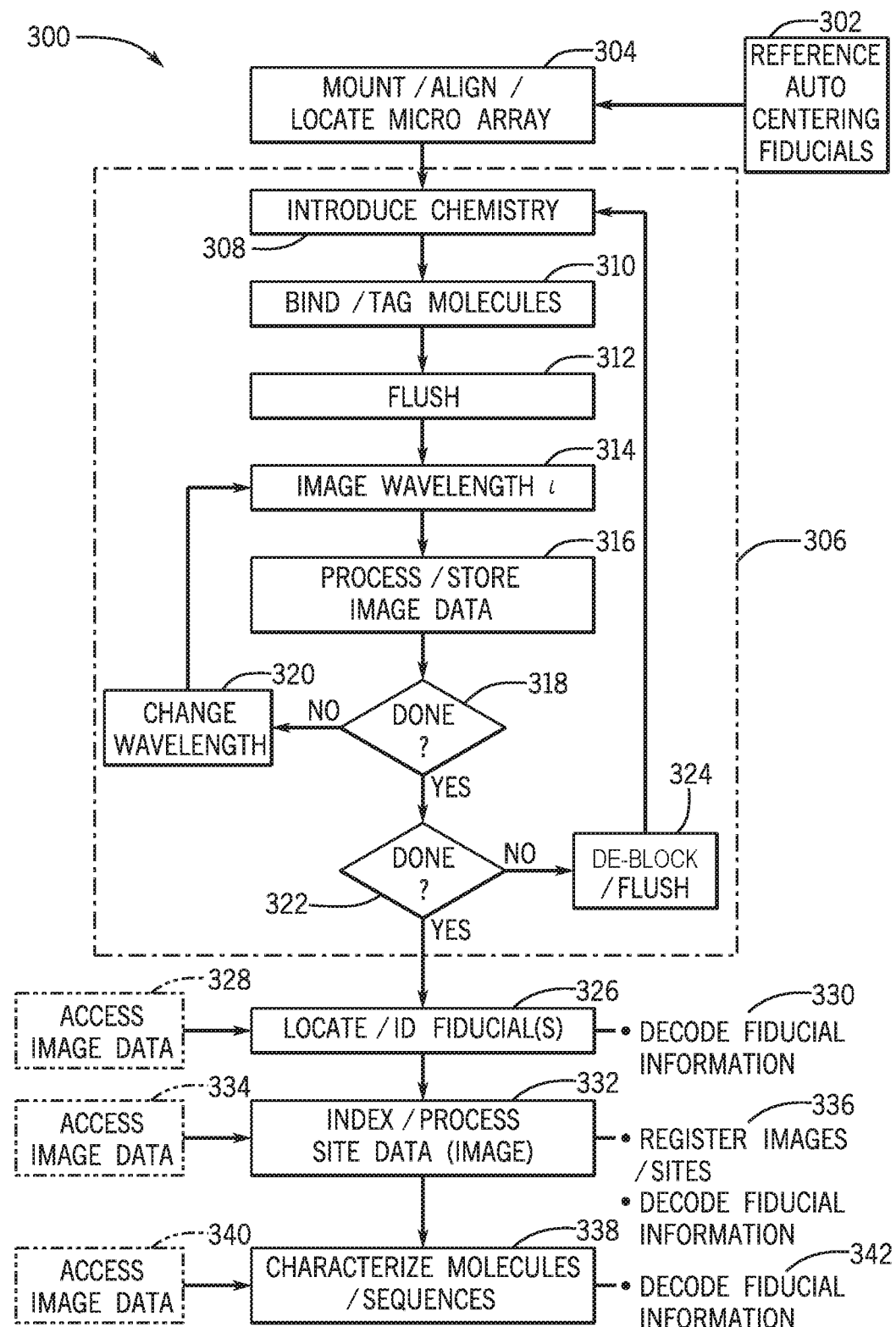
FIG. 23 is a flowchart illustrating example logic for using the fiducials set forth in the present disclosure.

As discussed throughout the foregoing disclosure, the novel configuration, formation, layout, and use of the fiducials may make processing of patterned arrays more effective, efficient or meaningful. Example logic for utilizing the fiducials is illustrated in FIG. 23. The logic, indicated by reference numeral 300, may begin with referencing course alignment or auto-centering fiducials as indicated at reference 302. As discussed above, the patterned array may be prepared in advance by obtaining samples or a library of molecules to be characterized, disposing or attaching them at sites in the patterned array, enhancing the detectability of the molecules (e.g., through amplification), preparing a flow cell for processing, and installing the flow cell in an imaging system, such as for sequencing. Block 302, then, may entail the detection of one or more fiducials that aid in properly locating and orienting the flow cell and array with respect to the imaging system, and the optics and translation stage used to progressively obtain image data. The auto-centering fiducials may comprise any of the forms and layouts discussed above, but will often include fiducials that lie outside of the regions of sites or swaths of sites.

The auto-centering fiducials are referenced during mounting, alignment and locating of the patterned array as indicated at 304 in FIG. 23. Thereafter, sequencing and imaging may be performed it as indicated by block 306. For many applications, this procedure may include multiple operations that may be cyclically repeated, such as for obtaining sequence information from templates or analytes comprising multiple bases of DNA (or other molecules). In the example logic of FIG. 23, for example, this process proceeds by introduction of the chemistry used to bind and tag molecules at the populated sites as indicated at 308, resulting in these molecules being bound and tagged as indicated at 310, so as to facilitate detection of the individual molecules that will return signals at the current cycle of the process. At 312, the flow cell may be flushed to remove remaining chemistry. At 314, then, the sites may be imaged at a desired wavelength as discussed above. The imaging may produce image data that are immediately (or subsequently) processed and stored, as indicated at 316. Such processing may include detection of signals returned from the sites by virtue of the tag molecules, indexing of the sites, maintaining or discarding any data that is useful or not useful, and so forth. At 318, it is determined whether another wavelength of radiation should be used for a further cycle of imaging, and as indicated at 320, if one or more other wavelength images are desired, the process returns to 314 for such imaging. Once this cycle of imaging is complete, it may be determined at 322 whether all desired imaging and sequencing have been completed. If not, a de-blocking and flushing process 324 may be implemented and new chemistry introduced to complete a further cycle of sequencing and imaging by returning to 308. Once all desired cycles are complete, the system may proceed to data processing.

The processing of the image data, stored on one or more memory circuits, may be performed locally or remotely. Moreover, the processing of the data may be done by the same system, or by another system, by accessing the stored image data or data derived from the image data (e.g., an indexed list of sites that returned signals during successive imaging). This processing may proceed by identification and localization of any fiducials that may be detected from the image data, as indicated at 326. For this purpose, the image data, or data derived from the image data, may be accessed as indicated at step 328, which may again be performed locally or remotely. The fiducials may be identified, located, and interpreted by any of the techniques discussed above, such as, depending upon their configuration, form, layout, and any information that they may encode. At this point, some of the information that may be encoded by the fiducials may be decoded as indicated by reference 330. Such information may include, for example, the location of the fiducial, the identification of the fiducial, determination of the location of other features (including other fiducials), identification of the array or any array-related information, and so forth.

At 332, then, the image data, including data indicative of the sites that return signals, the specific signals returned (e.g., at what wavelengths or frequencies), and their locations may be indexed and processed. Here again, this may entail accessing the image data or data derived from the image data, as indicated by 334. This access is represented in the figure as being repeated insomuch as 332 may be performed at the same time as 336, or at some later time or location. The process performed at 332 may include registration of images or sites or fiducials detected from the image data, and further decoding of fiducial information, and so forth.

At 338, then, molecules at sites that return or did not return signals at specific stages of the cyclic imaging may be characterized (such as by reference to the signals returned). This may also include accessing image data, or data derived from the image data, as indicated at 340. Moreover, this process may include logically assembling sequences of molecules at the individual sites, and assembling segments of molecules from different sites to obtain longer sequences. Here again, this process may include decoding further information from the fiducials at 342, such as identification of a subject (e.g., a donor of the sample), identification of a date or institution for which the process was performed, and so forth.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

All publications, patents, and patent applications cited in this specification are hereby incorporated by reference in their entirety.

The terms "substantially" and "about" used throughout this disclosure, including the claims, are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%. Furthermore, it is to be understood that the ranges provided herein include the stated range and any value or sub-range within the stated range. For example, a range represented by from about 5 μm to about 100 μm, should be interpreted to include not only the explicitly recited limits of from about 5 μm to about 100 μm, but also to include individual values, such as about 6 μm, 75 μm, 90.5 μm, etc., and sub-ranges, such as from about 15 μm to about 85 μm, etc.

In this disclosure, including the claims, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, § 2111.03.

While several examples have been described in detail, it is to be understood that the disclosed examples may be modified. Therefore, the foregoing description is to be considered non-limiting.

The invention claimed is:
1. An array, comprising:
   a support including a swath where reaction sites are located, each reaction site including an oligonucleotide probe that is to hybridize to a biological sample, the biological sample comprising a nucleic acid sequence that responds in successive cycles of fluorescent imaging; and
   six fiducial features formed in a hexagonal pattern on the support in the swath to define an image area, wherein each of the six fiducial features in the hexagonal pattern is a uniform distance from a center point of the image area, wherein each of the six fiducial features has a fluorescent material in a single circle shape that separates an inner area where some of the reaction sites are located and an outer area where some other of the reaction sites are located, wherein the fluorescent material responds in the successive cycles of fluorescent imaging, wherein the six fiducial features are disposed in rows that are offset with respect to one another, wherein in the offset rows, fiducials of a first row do not align with fiducials of an adjacent second row, relative to a line perpendicular to the first row and the adjacent second row, and wherein the some of the reaction sites in the outer area are positioned within the hexagonal pattern.

2. The array of claim 1, wherein the six fiducial features are disposed in a density to provide each of the six fiducial features in the image area.

3. The array of claim 1, wherein the fluorescent material of each of the six fiducial features is responsive to at least two different wavelengths of light to be used in the successive cycles of fluorescent imaging.

4. The array of claim 1, wherein each of the six fiducial features comprises a plurality of depressions arranged in the single circle shape and a plurality of objects disposed in the depressions, each of the plurality of objects comprising the fluorescent material.

5. The array of claim 1, wherein the reaction sites are disposed in a repeating pattern on the support.

6. The array of claim 1, wherein the support comprises a plurality of areas, each of the plurality of areas including a respective location, a respective oligonucleotide probe, and six fiducial features forming the hexagonal pattern around the respective location.

7. The array of claim 1, wherein at least one of the six fiducial features is structured to produce image data encoding information.

8. The array of claim 1, wherein the fluorescent material of each of the six fiducial features further comprises autofluorescent microspheres that return fluorescent signals during all phases of imaging at different wavelengths.

9. The array of claim 1, wherein the six fiducial features provide positioning information about the reaction sites.

10. A method, comprising:
disposing an oligonucleotide probe that is to hybridize to a biological sample at each of a plurality of reaction sites in a swath on a support, the biological sample comprising a nucleic acid sequence that responds in successive cycles of fluorescent imaging; and
disposing six fiducial features in a hexagonal pattern on the support in the swath to define an image area, wherein each of the six fiducial features in the hexagonal pattern is a uniform distance from a center point of the image area, each of the six fiducial features comprising a fluorescent material in a single circle shape that separates an inner area where some of the plurality of reaction sites are located and an outer area where some other of the plurality of reaction sites are located, wherein the fluorescent material responds in the successive cycles of fluorescent imaging, wherein the six fiducial features are disposed in rows that are offset with respect to one another, wherein in the offset rows, fiducials of a first row do not align with fiducials of an adjacent second row, relative to a line perpendicular to the first row and the adjacent second row, and wherein the some of the plurality of reaction sites in the outer area are positioned within the hexagonal pattern.

11. The method of claim 10, further comprising:
introducing the biological samples to the support, whereby the biological samples respectively hybridize to the probes; and
imaging the biological samples and the fiducial features in the successive cycles of fluorescent imaging at different wavelengths of light to produce image data that encodes fluorescent signals produced by the biological samples and the fiducial features.

12. The method of claim 11, wherein between each successive cycle of fluorescent imaging, a tag is removed from the biological samples at the reaction sites, and an additional biological component is added to the biological samples at the reaction sites, the additional biological components having tags that respond to the successive cycle of fluorescent imaging.

13. A method, comprising:
accessing image data encoding successive images of biological samples hybridized to the oligonucleotide probes of the array of claim 1;
registering, for the successive images, the reactive sites on the support by reference to the fiducial features; and
processing the registered successive images to transform data derived from the registered successive images to sequence data.

* * * * *